United States Patent [19]

Hilder et al.

[11] Patent Number: 5,306,863
[45] Date of Patent: Apr. 26, 1994

[54] TRANSFORMED PLANT WHICH EXPRESSES AN INSECTICIDALLY EFFECTIVE AMOUNT OF A BOWMAN-BIRK TRYSPIN INHIBITOR FROM VIGNA UNGUICULATA IN LEAVES, STEMS OR ROOTS, AND A METHOD FOR THE PRODUCTION THEREOF

[75] Inventors: Vaughan A. Hilder, Merryoaks; Angharad M. R. Gatehouser, Stanley; John A. Gatehouse, both of Stanley; Donald Boulter, Durham City; Richard F. Barker, Barhill; Michael Bevan, Norwich, all of Great Britain

[73] Assignee: Agricultural Genetics Company Limited, Cambridge, England

[21] Appl. No.: 997,911

[22] Filed: Dec. 29, 1992

Related U.S. Application Data

[60] Division of Ser. No. 656,039, Feb. 19, 1991, Pat. No. 5,218,104, which is a continuation of Ser. No. 492,337, Mar. 12, 1990, abandoned, which is a continuation of Ser. No. 134,842, Dec. 18, 1987, abandoned.

[30] Foreign Application Priority Data

Dec. 19, 1986 [GB] United Kingdom ................. 8630448
Nov. 2, 1987 [GB] United Kingdom ................. 8725610

[51] Int. Cl.$^5$ .................. A01H 5/00; A01H 4/00; C12N 15/00; C12N 15/09
[52] U.S. Cl. .................. 800/205; 435/172.1; 435/172.3; 536/23.6; 935/67
[58] Field of Search ............. 435/172.1, 172.3, 320.1, 435/91; 536/23.1, 23.6; 800/205, 230; 935/23, 91, 67

[56] References Cited

U.S. PATENT DOCUMENTS 4,640,836  2/1987  Boulter et al. .................. 424/195.1

FOREIGN PATENT DOCUMENTS 0135343  3/1985  European Pat. Off. ...... A01N 65/00
0142924  1/1986  European Pat. Off. ...... A01N 65/00
0193259  9/1986  European Pat. Off. ...... C12N 15/00

OTHER PUBLICATIONS

Richardson, M., *Phytochem.* (1977) 16:159–169.
Hammond et al, "Additions and Corrections", *J. Biol. Chem.* (1985) 260:7806.
Liener et al, *Toxic Constituents of Plant Foodstuffs*, Chap. 2, pp. 7–71.
Johnson et al, "Expression of Proteinase Inhibitors ...".
Odani et al, *J. Biochem.* (1976) 80:641–643.
Journal of Biological Chemistry, 1984, vol. 259, R. W. Hammond et al., "Molecular cloning and analysis of a gene coding for the Bowman Birk Protease inhibitor in Soybean", pp. 9883–9890.
Journal of Cellular Biochemistry Supplement, 1983, No. 7 part B Abstract 1230 D. E. Foard et al., "Potential use of some seed proteins as factors in Host Pathogen predator relationships", p. 273.
Handbook of Chemical Synonyms and Trade Names, p. 174.
Lee et al. (1986) Proc.-Nat. Acad. Sci. vol. 83 pp. 7277–7281.
Keil et al (1986) Nuc. Acid. Res. vol. 14, #14, pp. 5641–5650.
Hilder et al. (1987) Nature 330, pp. 160–163.
Gatehouse et al. (1980) Phytochemistry vol. 19: pp. 751–756.
Foard et al. (1983) Plant Molecular Biology, pp. 223–233.
Dietrich et al. (1990) Ph. Mol. Biol. 15: pp. 207–223.

*Primary Examiner*—Gary Benzion
*Attorney, Agent, or Firm*—Oblon, Spivak, McClelland, Maier & Neustadt

[57] ABSTRACT

The invention relates to a recombinant DNA molecule which comprises a structural gene coding for a trypsin inhibitor, in particular a trypsin inhibitor from a legume, more particularly from *Vigna unguiculata* (cowpea trypsin inhibitor or CpTI), or for a protein having properties resembling those of CpTI and/or having a substantial degree of homology therewith.

The invention also relates to a recombinant DNA plasmid comprising such a DNA molecule, and to the incorporation of the DNA into the nuclear genome of a plant.

21 Claims, 6 Drawing Sheets

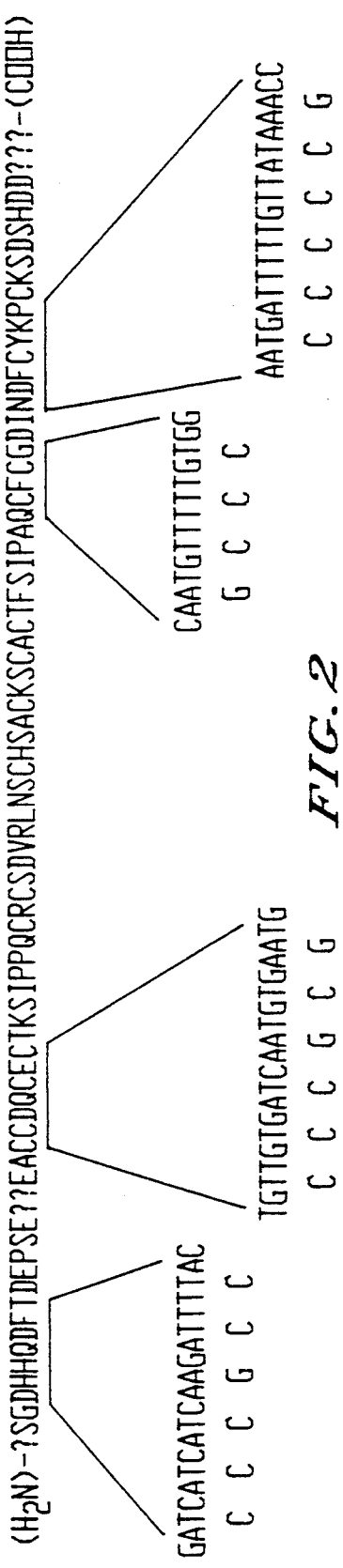

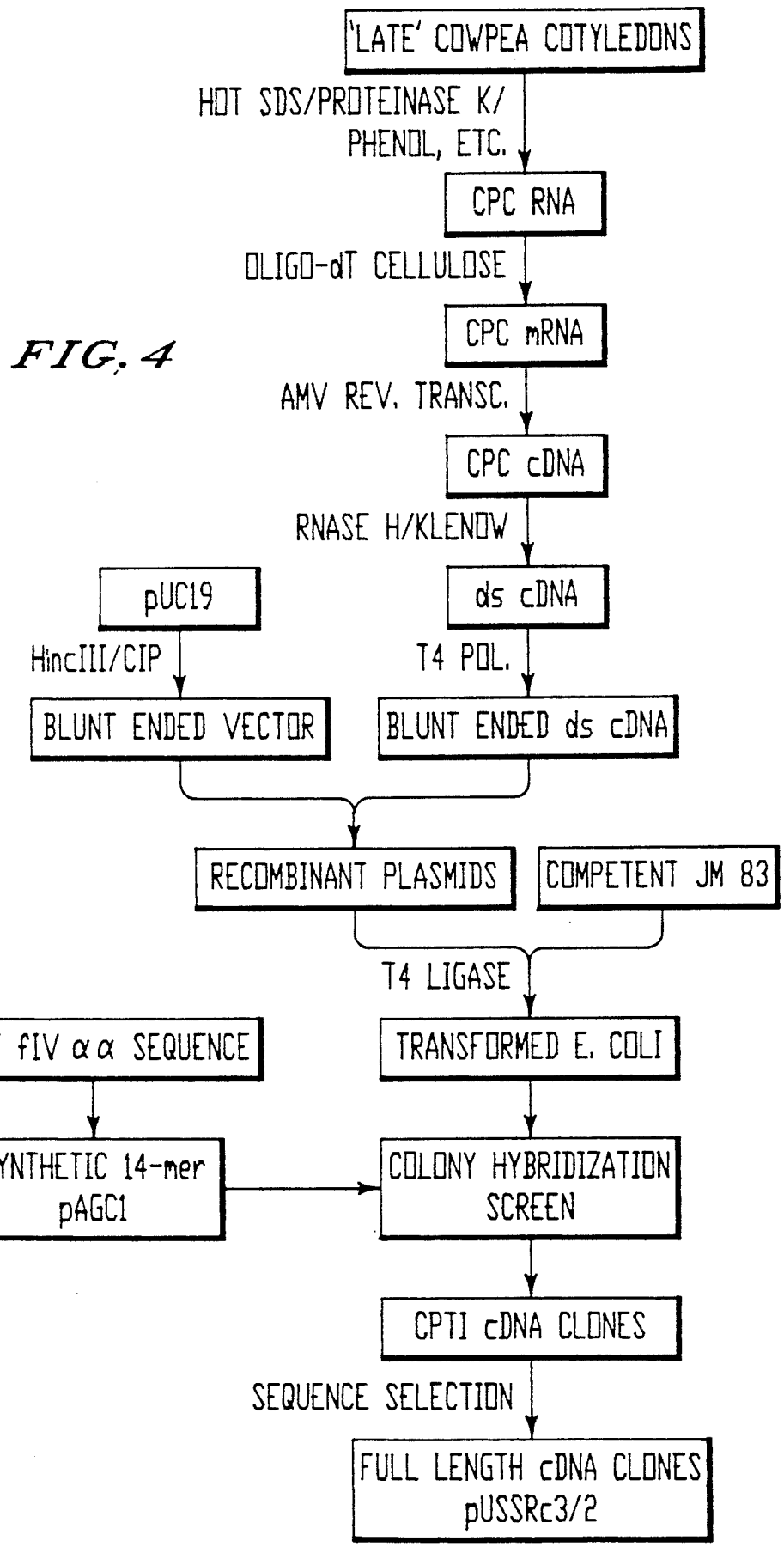

GATGGCAAACATAGTACTATTATTTGATTTGTAATATGTACATAAAGAGCAGTGAGACTAAGCCA
ATAACATCAGAAAATAAAAACTCAGGTACATTGACATTTATTCACCTTACACTGCAAAAACAAAA
AACTCTCAAGTTTGAAAACAAGATGATGGTGCTAAAGGTGTGTGTGCTGGTACTTTTCCTTGTAG
GGGTTACTACTGCAGCCATGGATTTGAACCACCTCGGAAGTAATCATCATGATGACTCAAGCGAT
GAACCTTCTGAGTCTTCAGAACCATGCTGCGATTCATGCATCTGCACTAAATCAATACCTCCTCA
ATGCCATTGTACAGATATCAGGTTGAATTCGTGTCACTCGGCTTGCAAATCCTGCATGTGTACAC
GATCAATGCCAGGCAAGTGTCGTTGCCTTGACATTGCTGATTTCTGTTACAAACCTTGCAAGTCC
AGGGATGAAGATGATGAGTAAGAAAAAGGAAGATGAAGTCTCTCTCAGATGAATAAAGCCCTTGA
GTTTTGTTTGTTGTGTAAGGGAAGACAGAATAAAAGTTGGAATAAAAGCTAGTGCTGTTCATC

FIG. 6

GATGCACACCAAGCCCGAGCCTTCTGGGGACTTGTAGTGCTAGCTTGAAGGTGTCTGAGGTAGGT
CAAGTCATCAAAAGTGGTGATCATCATGAAGCAACTGATGAGCCCTCTGAATCTTCAGAAGCATG
CTGTGATCGTAGCGAATGCACAAAATCAATACCTCCTCAATGCCGCTGTTCAGACGTAAGGCTCA
ATTCGTGCCATTCAGCTTGCAAATCATGTGCCTGCACATTTTCCATTCCTGCACAGTGTTTTTGT
GGTGACATAAACGACTCCTGCTATAAACCTTGCAAGTCCTCCAGTCATGATGATGATGACTGGGA
TAAGTAAYGAACAAGTTTAATGTAAGCTCTCTCTAAATGGATGAAGCCCTTTCGGGCTTTGTTCG
TTGTGTAATGAGATCAATAAACTTTGAATAAAAGCTCTTGTTTTCGTGCC

FIG. 7

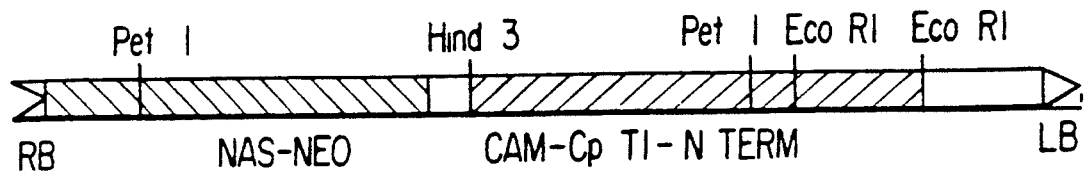
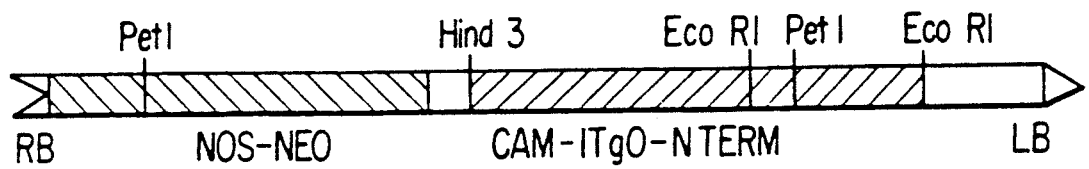
FIG. 9A
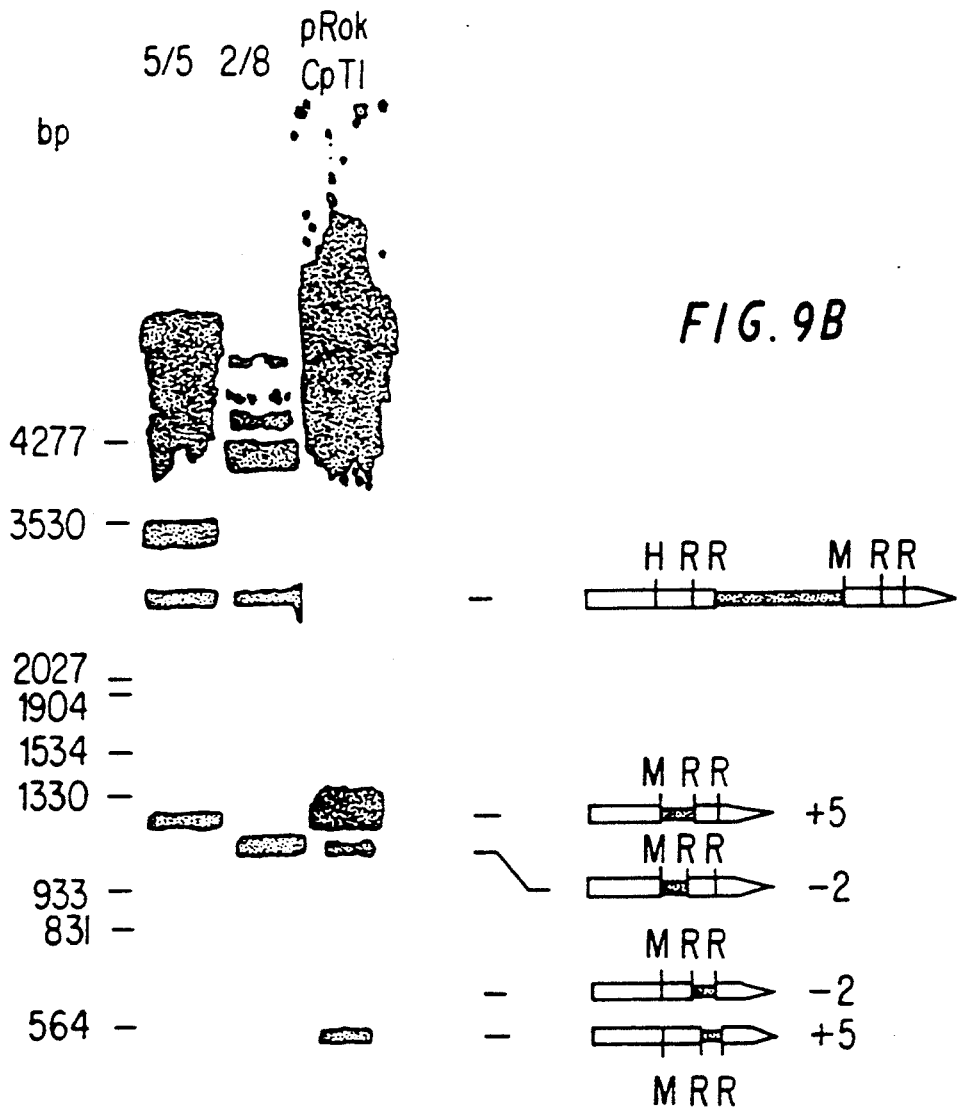
FIG. 9B

TRANSFORMED PLANT WHICH EXPRESSES AN INSECTICIDALLY EFFECTIVE AMOUNT OF A BOWMAN-BIRK TRYSPIN INHIBITOR FROM VIGNA UNGUICULATA IN LEAVES, STEMS OR ROOTS, AND A METHOD FOR THE PRODUCTION THEREOF

This is a division of application Ser. No. 07/656,039, filed Feb. 19, 1991, now U.S. Pat. No. 5,218,104, which is a continuation of application Ser. No. 07/492,337, filed Mar. 12, 1990, abandoned, which is a continuation of application Ser. No. 07/134,842, filed Dec. 18, 1987, abandoned.

This invention relates to the protection of plants against their pests through plant genetic engineering. It is especially concerned with the protection of cotton and cereal crops by the transfer into plants of specific genes coding for insect resistance, but it is also applicable to other crops for which field and storage pests constitute a serious economic problem. Such crops include cotton, maize, rice, soybeans, sugar beet, wheat, fruit, vegetables and vines. In particular, this invention relates to genes for trypsin inhibitors derived from legume plants, especially the cowpea trypsin inhibitor (CpTI).

Insect pests of crops cause losses averaging from 5 to 15% of the annual agricultural production. The monetary value of these losses has been estimated at several billion dollars per year and in addition there is an annual expenditure for pesticides and for spraying and dusting equipment. For example, the cotton crop is highly susceptible to certain pests, including insects. In the U.S. alone, at least 125 insect species cause economic damage to cotton. Cotton insecticide accounts for the largest proportion of global insecticide usage at $1335 million (in 1985), which is equivalent to 31% of the total expenditure. In the U.S., annual losses average $500 million and in addition growers spend nearly as much on insecticides and application in an effort to keep yields profitable. Pests attack cotton from seed to harvest. Generally, those pests attacking at the early stage affect yield, whereas those attacking at later stages affect quality.

One major group of cotton pests are the bollworms of the genus Heliothis (including *H. virescens, H. armigera* and *H. zea*. The Heliothis bollworms infest a wide range of plant families in addition to cotton, they attack many cereals such as maize and sorghum, as well as other crops including tobacco, phaseolus bean, soybean and sunflower. Another serious pest of cotton is the pink bollworm (*Pectinophora gossypiella*) which worldwide is its most important pest and in developing countries can destroy up to 70% of the crop. Other serious pests are the boll weevils (Anthonomus spp. including *A. grandis*). The larvae of Heliothis, Pectinophora, and Anthonomus severely reduce cotton yields since they feed within the cotton squares (buds) and bolls, resulting in death and shedding of the squares, and small bolls. In the larger bolls the lint becomes stained and decayed. Another insect genus presenting a serious problem in cotton is the genus Spodoptera including *S. litura* (the rice cutworm or fall armyworm) and *S. littoralis* (the cotton leafworm). Spodoptera is also a pest of maize, rice, sorghum and tobacco.

Another major crop in which insect damage reduces yields is maize. The total world expenditure on insecticides for use in maize was $470 million in 1985. In the U.S. alone, insect damage is estimated to be greater than $900 million annually. The corn rootworm (Diabrotica spp.) is a serious pest and, in the U.S., yield losses have been calculated at 10–30%. Another destructive pest of maize in the U.S. is the European corn borer (*Ostrinia nubilalis*) where the first generation of borers feed on the leaves and stalks, thus starving the ears of nutrients. Annual losses from the corn borer in the U.S. for the 1970-75 period have been calculated at $310 million per annum. Other important pests of maize include *Sitophilus oryzae* (the rice weevil), the corn earworm (*H. zea*) which causes losses in the U.S. estimated at between $75 to $140 million annually, the spotted stalk borer (*Chilo suppressalis*) and the cutworms (Agrotis spp.) which also attack cotton, tobacco and many vegetables.

In spite of the availability of a wide range of chemical pesticides, insect pests remain a serious problem. Many pesticides have the severe disadvantages of high toxicity towards humans and wildlife and relatively high phytotoxicity. Insect resistance to chemical pesticides is also an increasing problem.

Plant breeders have also attempted to reduce losses caused by insect attack by incorporating insect resistance genes into their varieties in conventional breeding programmes. Most plants show resistance to most insects, resistance can be physical or chemical. For example, the hairs on the leaves of many plants can stop small insects from getting near enough to the surface to chew it. In other oases plants use a range of complex secondary chemicals to make their tissues unattractive or toxic. These types of resistance are likely to be under the control of many genes, and so are difficult for the plant breeder to exploit. Often resistant varieties have shown a yield depression and so have not been economically viable. This is presumably because the specific character of insect resistance has been associated with other detrimental characters and it has not been possible to separate easily the two effects.

Recent developments in plant biotechnology now offer the prospect of broadening the scope of plant improvement through the addition to existing germplasm of genes coding for specific characters. Research is being undertaken on the isolation and transfer of genes for herbicide resistance, disease resistance, aspects of product quality; and resistance to insects.

It has been argued that genetically-engineered insect-resistant plants would have several advantages over the use of chemical pesticides (for a discussion see report in Agrow [1986] (29). These advantages include:

a) season long protection
b) insects are always treated at the most sensitive stage
c) protection independent of the weather
d) protection of difficult to treat plant tissues
e) only crop-eating insects are exposed
f) material confined to plant tissues
g) active factor is biodegradable and non-toxic.

However there are also several possible limiting factors:

1. PLANT SPECIES AMENABLE TO TRANSFER

Although this is a key factor, it is likely that the technology to transform major food crops will shortly be in place. The recent report on cotton transformation (Umbeck, P., Johnston, G., Barton, K., Swain, W., [1987] Genetically transformed cotton (*Gossypium hirsutum* L.) plants. Bio/Technology 5, 263–266) and the claims for maize transformation indicate that the large investment in transformation research will soon give suitable protocols.

SPECTRUM OF ACTIVITY AGAINST PESTS

Generally insecticides have a broad spectrum of activity against insect pests. Biological pesticides incorporated into crops through genetic engineering would need to have a wide enough spectrum of activity to make their use worthwhile.

Patent applications have been filed on the use of the *Bacillus thuringiensis* (Bt) crystal protein gene to produce insect resistance plants (EPO Applications 84306494.0 and 86300291.1). However, in the case of EPO Application 84306494.0, the specification teaches only that tobacco hornworms (*Manduca sexta*) "fed on transformed tobacco callus tissue containing the plant expressible full-length insecticidal protein gene were observed to display symptoms attributable to *B. thuringiensis* crystal protein toxicity". No information on insecticidal effects of plants containing the gene was presented. Application 86300291.1 does give information on the effects of a Bt gene in transgenic tobacco plants, but again the data is restricted to one insect only, the tobacco hornworm.

One potential disadvantage of inserting Bt into plants in order to increase insect resistance is that different strains of the bacterium make toxins with different specificities. This might mean that it will be necessary to combine several Bt genes in order to make a crop resistant to a sufficiently wide spectrum of insect pests.

3. NEGATIVE SIDE EFFECTS

It will be important that transgenic plants containing insect resistance genes do not suffer any appreciable yield penalty.

There has been some concern about the possible environmental effects of incorporating an insect resistance gene into crop plants such that pests are presented with an "in-built insecticide" continuously. It could be argued that this would place a very high selection pressure on the pests and hasten the development of resistance. However, one counter to that argument is that trypsin inhibitors act directly on the active site of a major digestive enzyme. The chances of development of resistance by insects through viable mutation of the target site would seem to be low. Resistance could probably only be built up through complex, multiple changes in the insects' metabolism such that the inhibitor was detoxified before it could do damage.

There has been considerable speculation in the literature suggesting that plants contain a variety of proteins that may confer resistance to pathogens or insect predators by inhibiting their digestive or other enzymes (Ryan, C. A. [1983] Insect-induced chemical signals regulating natural plant protection responses. In: Denno R. F. & McClure M. S. (eds). Variable Plants and Herbivores in Natural and Managed Systems, pp 43-60, Academic Press).

It has previously been shown that naturally occurring trypsin inhibitors present only at one particular stage in plant development, namely the mature seed, can exhibit a powerful toxicity towards a wide variety of pests of other plants when incorporated into artificial diets. Surprisingly, when the gene for a trypsin inhibitor is transferred into another plant species in such a way that it expressed throughout plant development, the insect resistance of the transgenic plants is increased significantly. Thus it should be possible to transfer specific genes coding for resistance to a wide spectrum of insect pests into otherwise agronomically desirable genotypes of crop plants.

Recent evidence suggests that protease inhibitors are part of the complex interaction between plant nutritional value and the insect's digestive physiology (Broadway, R. M., Duffey, S. S. Pearce, G , Ryan, C. A. [1986] Plant proteinase inhibitors: A defense against herbivorous insects? Ent. Exp. Appl. 41, 33-38). However, until now there has been no conclusive demonstration that protease inhibitors do indeed increase insect resistance when expressed in plants.

The present invention relates to recombinant DNA molecules encoding members of a legume trypsin inhibitor polypeptide. More particularly, the invention relates to recombinant DNA plasmids carrying coding sequences for trypsin inhibitor genes from *Vigna unguiculata* (cowpea, otherwise known as the black-eyed pea, black-eyed bean, kaffir bean, Hindu cowpea and yard-long bean), the production of the same and the use of the same for transferring the character of cowpea trypsin inhibitor (CpTI) expression to other species of plants for the purpose of enhancing their resistance to various species of insect pests.

Previous experiments have established that the amount of CpTI present in *V. unguiculata* seeds is related to the resistance of *V. unguiculata* to attack by the bruchid beetle (Gatehouse, A. M. R., Gatehouse, J. A., Dobie, P., Kilminster, A. M., Boulter, D., [1979] Biochemical basis of insect resistance in *Vigna unguiculata* J. Sci. Food Agric. 30, 948-958; Gatehouse, A. M. R., Boulter, D., [1983] Assessment of the antimetabolic effects of trypsin inhibitors from cowpea (*Vigna unguiculata*) and other legumes on development of the bruchid beetle *Callosobruchus macalatus* J. Sci. Food Agric. 34, 345-350). The use of the trypsin inhibitors which occur naturally in *V. unguiculata* to protect plants against invading insect pests by a method in which the insect is presented with pesticidally effective amounts of one or more of the trypsin inhibitors from *V. unguiculata* has been described in U.S. Pat. No. 4.640.836 (granted 3 Feb. 1987). That patent reports that purified CpTI is active against the following Lepidopteran pests: *Heliothis virescens* (tobacco budworm); *Spodoptera littoralis* (cotton leafworm); *Chilo partellus* (spotted stalk borer); *Heliothis armigera* (American bollworm) and the Coleopteran pest *Tribolium confusum* (flour beetle). The information published on the effects of CpTI against insect pests in artificial diet studies is summarised in Table 1. The present invention provides DNA molecules which encode the genetic information required for the production of CpTIs in genetically engineered organisms.

Any genetically-engineered crop plant containing the CpTI gene would need to be safe to man and to the environment. There are several reasons to suggest that the CpTI gene would be safe.

The cowpea is a major food crop in several regions of the world (Singh, S. R., Rachie, K. O. [1985] Cowpea research, production and utilization. Wiley). Although normally cooked, it can be eaten raw.

Furthermore, in the human digestive tract (and also that of other mammals), Proteins are broken down by several different types of enzymes. CpTI is very sensitive to inactivation by pepsin (A. Gatehouse, unpublished results) and preliminary data from rat feeding trials indicated that rats fed on diets containing a CpTI did not show reduced weight gain (D. Boulter, unpublished results).

TABLE 1

| Insecticidal activity of CpTI in artificial diet studies. | | | |
|---|---|---|---|
| Insect | Common Name | Crop Species attacked | Reference |
| Lepidopteran Pests | | | |
| *Chilo partellus* | Spotted Stalk Borer | Maize, Sorghum Sugarcane and Rice | U.S. Pat. No. 4,640,836 |
| *Heliothis armigera* | American Bollworm | Cotton, Beans, Maize and Sorghum | U.S. Pat. No. 4,640,836 |
| *Heliothis virescens* | Tobacoo Budworm Budworm | Cotton, Tobacoo | U.S. Pat. No. 4,640,836 |
| *Heliothis zea* | Corn Earworm Cotton Bollworm | Maize, Cotton Beans and tobacco | U.S. Pat. No. 4,640,836 |
| *Spodoptera littoralis* | Cotton Leafworm | Cotton, Tobacco Maize and Rice | U.S. Pat. No. 4,640,836 |
| Coleopteran Pests | | | |
| *Tribolium confusum* | Flour Beetle | Most flours | U.S. Pat. No. 4,640,836 |
| *Callosobruchus maculatus* | Cowpea Bruchid | Cowpea, Soyabean | Gatehouse and Boulter [1983] |

The prime object of the present invention is to provide recombinant plasmid constructs containing the complete coding sequences of CpTI genes within vectors which permit their introduction into target plant species and facilitate selection of recombinant plants and permit expression of the introduced gene within those plants, such plants being transformed to enhanced resistance to insect pests by virtue of the presence of the CpTI polypeptide within their tissues.

The present invention provides a DNA molecule which comprises a structural gene coding for a trypsin inhibitor, preferably a trypsin inhibitor derived from a legume, in particular from *V. unguiculata* (cowpea trypsin inhibitor or CpTI), or for a protein having properties resembling those of CpTI and having a sufficient degree of homology to be generally accepted as a member of the CpTI family on normal scientific criteria.

Reference is now made to the accompanying drawings, in which:

FIG. 1 shows the amino acid sequences of Bowman-Birk trypsin inhibitors from cowpea;

FIG. 2 shows the amino acid sequences of CpTI fIV and predicted possible coding sequences for the regions most suitable for specifying synthetic mixed oligonuclectide probes for CpTI cDNAs;

FIG. 3 shows the nuclectide sequence of the coding strand of the insert in pAGC1;

FIG. 4 shows the strategy for isolation of full-length cDNA clones corresponding to CpTI;

FIG. 6 shows the nuclectide sequence of the coding strand of the insert in pUSSR c3/2;

FIG. 7 shows the nuclectide sequence of the coding strand of the insert in pUSSR d4/6;

FIGS. 9A and 9B is a Southern blot analysis of genomic organisation of transformed sequences in +5/5 and −2/8.

Figure 5:
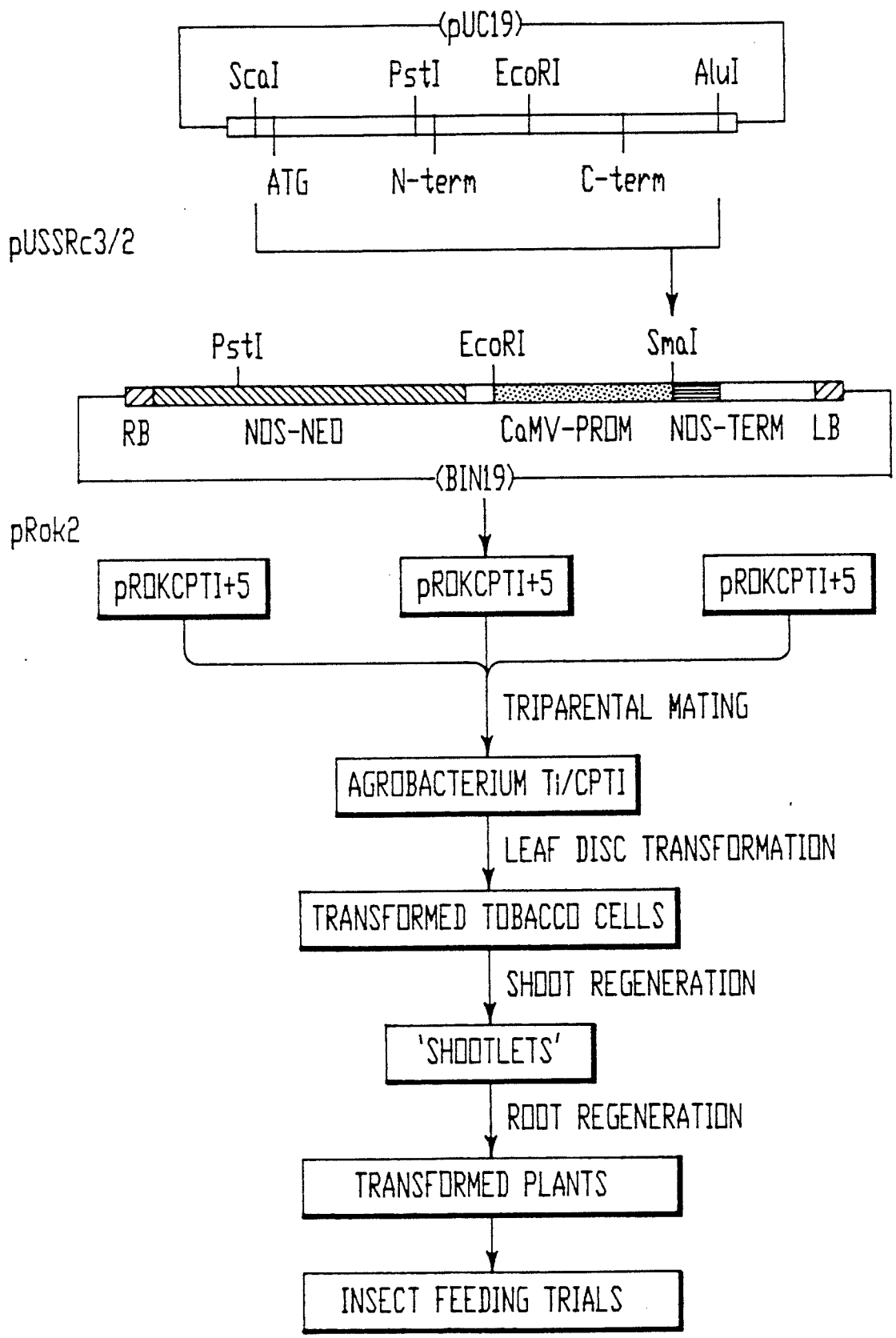
FIG. 5 shows the strategy for transformation of tobacco plants with pUSSRc3/2 construct in pROK2 vector.

The Bowman-Birk type trypsin inhibitors of *V. unguiculata* are encoded by a moderately-repetitive family of genes which are expressed in cowpea cotyledons as four iso-inhibitors separable by ion exchange chromatography. All four iso-inhibitors have similar trypin inhibitory activities as measured by in vitro enzyme inactivation assays:

| | Total | fI | fII | fIII | fIV |
|---|---|---|---|---|---|
| Relative inhibitory activity | 1.00 | 1.07 | 1.14 | 1.05 | 0.7 |

The major iso-inhibitor of the cowpea is fIV. These genes have sufficient homology to cross hybridize with CpTI full length cDNA probes in 0.45M NaCl, 0.045M Na citrate (3×SCC) at 68° C. Examples of the fIV iso-inhibitor primary sequence (determined by protein sequencing (Sammour, R. H. A. [1985], Ph. D. thesis, University of Durham, U.K.) or predicted from CpTI cDNA sequencing) are presented in FIG. 1. Other members of the *V. unguiculata* family of trypsin inhibitor polypeptides constitute variants of these sequences in which protease inhibitory activity is unimpaired.

FIG. 1 shows the following:

a) CpTI fIV major iso-inhibitor. (The blocked amino terminus, internal residues 15 & 16 and the carboxy terminus could not be determined).

b) CpTI cDNA d4/6 predicted sequence c) CpTI cDNA c3/2 predicted sequence

Sequences are presented in the single letter code of Dayof (Atlas of Protein Sequence and Structure, Vol.5, [1972] Nat.Biomed. Res. Foundation, Washington D.C., U.S.A.).

The trypsin inhibitor genes of cowpeas are expressed in the cotyledons late on during their maturation. The cowpea trypsin inhibitor proteins therefore have to be isolated from maturing seeds. The unusually high degree of cross linking in these proteins renders them poorly antigenic and methods for the identification and isolation of the corresponding genes which rely on the use of antibodies are, therefore, inefficient. The amino-acid sequence of the major trypsin inhibitor from *V. unguiculata* was used to predict the possible nucletide sequences of its messenger RNA. Four regions of this polypeptide comprise runs of four or more consecutive residues each of which can be encoded by no more than two alternative codons in messenger RNA. Such regions were found to be suitable for the specification of mixed sequence oligonuclectide probes covering all coding possibilities and of sufficient length to be reasonably specific for the gene in question, as indicated in FIG. 2.

Accordingly, polyadenylated RNA purified from "late" stage cotyledons of *V. unguiculata* was isolated.

Initially, mRNA was copied into complementary DNA in a conventional reverse transcription reaction. Second strand synthesis was carried out on the self-primed cDNA using the Klenow fragment of DNA polymerase I. Terminal loops in the double-stranded cDNA were removed by treatment with S1 nuclease and the ends of the molecules repaired in a "polishing" reaction with the Klenow fragment.

Synthetic octanuclectide Bam HI linkers with the sequence 5'-d(GGGATCCC) were ligated to the polished ds cDNA and extensively digested with Bst I (an isoschizomer of Bam HI). Linkered ds cDNA was ligated, using T4 DNA ligase, to the Plasmid pBR322 which had previously been linearised with Bst I and partially dephosphorylated by treatment with calf intestinal phosphatase (to reduce self-ligation of the vector ends).

The products of this ligation reaction were used to transform competent *E. coli* strain 910 to ampicillin resistance (this character is carried by the plasmid vector). Recombinants were identified by their sensitivity to tetracycline (the tetracycline resistance gene of pBR322 being inactivated by insertion of DNA into the Bam HI site).

Recombinants were screened for CpTI sequences by in situ colony hybridization according to the procedures of Grunstein and Hogness (Grunstein, M. & Hogness, D. S. [1975], Proc. Natl. Acad. Sci. U.S.A. 72, 3961], with the $^{32}$P-labelled, mixed, synthetic oligonuclectide

(the second line of bases refers to alternative bases at that nuclectide) corresponding to the 16 alternative 14-mers complementary to the sequence in region C of FIG. 2. This probe positively labelled about 14% of the clones, some of which were subsequently shown definitely not to be derived from trypsin inhibitor message. The 14-mer positive clone containing plasmid pAGC1, however, was unambiguously identified as containing a partial CpTI message by determination of the nuclectide sequence of the insert in the Bam HI site after transfer to the viral vector M13mp9 and sequencing using the established M13 dideoxy chain-termination procedure. The predicted amino-acid sequence from the only long open reading frame in this insert shows considerable homology with the major CpTI primary sequence and with the published primary sequences of other legume Bowman-Birk type trypsin inhibitors (Shimokawa, Y., Abe, O., & Kuromizu, K., [1984] Phylogenetic relationship of legume double-headed proteinase inhibitors. Nature & Culture 11, 39–45). The sequence showed a 65% homology with the corresponding region of the published sequence of the soybean SB1 gene coding sequence (Hammond, R. W, Foard, D. E. & Larkins, B. A., [1984] Molecular cloning and analysis of a gene coding for the Bowman-Birk protease inhibitor in soybean. J. Biol. Chem. 259, 9883–90).

The plasmid pAGC1 contains sequences derived from CpTI mRNA including 183 bp of coding sequence, comprising the sequence shown in FIG. 3. This sequence encodes the C-terminal half of a CpTI. This invention requires a complete coding sequence of a CpTI and so a new library was prepared using a high-efficiency cDNA cloning protocol and utilizing both the synthetic oligonuclectide and pAGC1 as probes as outlined below and illustrated in FIG. 4.

Cowpea cotyledon mRNA was copied into cDNA by reverse transcriptase in the presence of human placental RNase inhibitor. Second strand synthesis was effected by nuclease free DNA polymerase I in the presence of RNase H. The ends of the double stranded cDNA were rendered flush by digestion with T4 DNA polymerase. The reaction products were blunt-end ligated to the plasmid pUC19 which had been linearised with restriction endonuclease Hinc II and dephosphorylated with calf intestinal phosphatase. This ligation mixture was used to transform competent *E. coli* strain JM83 to ampicillin resistance. Recombinants were detected as white colonies on YT-Amp-BCIG-agar plates and were picked and grown on replicate nitrocellulose filters on YT-Amp-agar.

One of these recombinants, designated pUSSRc3/2, was identified as a (near) full length copy of a CpTI message sequence by:

i) Strong cross hybridization in in situ colony hybridization with the Bam HI insert of pAGC1.
ii) Weak, but positive, cross hybridization of the inserted fragment with the synthetic mixed 14-mer.
iii) The size of the insert in pUSSRc3/2 was measured as 582 bp, compared with the size of CpTI mRNA, measured from Northern blots of cowpea cotyledon total RNA probed with the pAGC Bam HI insert, of 550±50 nuclectides.
iv) The sequence of the inserted fragment was determined by established chemical sequencing procedures (Maxam, A. M. & Gilbert, W ,[1980] Sequencing end-labelled DNA with phase-specific chemical cleavages. Meth. Enz. 65, 499–560]. It was entirely homologous to the insert in pAGC1 over the length of the latter. The predicted amino acid sequence from its only long open reading frame showed a high degree of homology with legume trypsin inhibitors over the region corresponding to the mature protein. The sequence extends a few base-pairs 5' - to an in phase ATG - (methionine)-translation initiation codon.

The plasmid pUSSRc3/2 contains sequences derived from (almost) all of a CpTI mRNA, including the entire coding region for the precursor and mature proteins and the 3'- untranslated region, comprising the sequence shown in FIG. 6.

The plasmid pUSSRd4/6 contains the entire coding sequence of a mature protein of a different iso-inhibitor but lacks the natural translation initiator ATG codon and, therefore, an unknown amount of leader peptide sequence. It comprises the sequence shown in FIG. 7.

The CpTI sequence was transferred from the *E. coli* cloning vector pUC19 to an *Agrobacterium tumefaciens* Ti plasmid, plant transformation vector as outlined below and in FIG. 5.

Plasmid pUSSRc3/2 was digested with the restriction endonucleases Sca I, Alu I and Xmn I and the blunt ended, 550 bp long fragment was isolated from a polyacrylamide gel electrophoretic separation of the digestion products. This fragment contained the entire CpTI coding sequence, terminating 20 bp 5' - to the ATG-translation initiation codon and 92 bp 3' - to the TAA translation termination codon. This fragment was blunt-end ligated into the Sma I site of plasmid pRok2.

Plasmid pRok2 is an *Agrobacterium tumefaciens* Ti plasmid binary system vector designed and constructed by Dr. M. Bevan and Dr. T. Kavanagh specifically for the purpose of allowing cloned cDNA sequences to be transferred to and constitutively expressed in plants. It was derived from Bin 19 (Bevan, M. W. [1984], Binary Agrobacterium vectors for plant transformation. Nucl. Acids Res. 12, 8711–21) by inclusion between the right and left T-DNA border regions of an expression cassette comprising an 800 bp fragment from the cauliflower mosaic virus genome containing the CaMV 35S RNA promoter and a 250 bp fragment from the Agrobacterium T-DNA nopaline synthase gene containing its transcription termination and mRNA polyadenylation signals. These elements were incorporated into the binary Ti expression vector pRok1 (Baulcombe, D. C., Saunders, S. R., Bevan, M. V., Mayo, M. A. & Harrison, B. D. [1986] Expression of biologically active viral satellite RNA from the nuclear genome of transformed plants. Nature, 321, 446–9) from which pRok2 differs primarily in having a polylinker cloning site between the promoter and terminator fragments. This polylinker includes the Sma I site into which the CpTI cDNA fragment was inserted. These sequences confer constitutive initiation of transcription 10 bp upstream of the insert, and polyadenylation of the transcript 200 nuclectides downstream of the insert, in transformed plant cells.

The pRok-CpTI constructs were cloned into competent *E. coli* strain MC1022 and transformants were selected by their resistance to kanamycin. The identity of the constructs was verified by restriction analysis of plasmid DNA mini-preps from individual clones. Clone pRok-CpTI+5 contained the CpTI insert in the correct orientation for expression of the CpTI polypeptide, i.e.:

CaMV-PROM - 5'-CpTI-3' - NOS-TERM clone pRok-CpTI-2 contained the CpTI insert in the reversed orientation, i.e.:

CaMV-PROM - 3'-CpTI-5' - NOS-TERM and served as a control.

The T-DNA(L)/NOS-NEO/CAMV-PROM:CpTI:-NOS-TERM/T-DNA(R) constructs were transferred to *Agrobacterium tumefaciens* Ti plasmids in a triparental mating between: *Agrobacterium tumefaciens* LBA4404 harbouring the Ti plasmid pAL4404, *E. coli* HB101 harbouring pRok-CpTI+5 or pRok-CpTI−2 and *E. coli* HB101 harbouring the mobilizing plasmid pRk2013.

Transconjugants were selected by their ability to grow at 30° C. in the presence of kanamyoin, streptomycin and rifamycin on minimal agar Plates. To ensure freedom from non-resistant bacteria, the resistant colonies were streaked twice more on selective plates.

Agrobacteria harbouring CpTI+5 and CpTI−2 containing Ti plasmids were used to transform leaf discs of *Nicotiana tabacum* (cv. Samsun NN) and *N. plumbaginifolia* as illustrated below and in FIG. 5. Transformants were selected by their resistance to kanamycin, confered by the NOS-NEO gene in the constructs. Transformed plants were regenerated from shootlets by transfer to a root-inducing, kanamycin containing agar medium. Rooted plants were grown on in pots of Perlite/compost in a Sherer growth cabinet.

Insect resistance of the plants was tested by inoculating the individual plants with young larvae of *Heliothis virescens* and measuring the extent of damage caused to the plants and the growth and survival of the insects with time. *H. virescens* was used as it is a commercially important pest of both cotton and tobacco in the U.S.A. Young larvae less than 24 h old, 1–2 mm in length, were used.

The level of resistance to insect attack which has been determined for the plants transformed with the CpTI+5 construct shows a considerable overlap with that of the control plants (Table 2). On an individual plant basis, however, approximately 1 in 5 of the CpTI+5 transformants (*N. tabacum* +5/5, +5/21 and +5/D4; *N. plumbaginifolia* +5/T104 and +5T109 in particular) showed a clear and consistent increase in resistance to damage by *H. virescens* larvae and reduced survival and development of insects on the plant (Table 4).

It has been demonstrated that these resistant plants are expressing a CpTI-like protein in immunobinding ELISA assays. Anti-CpTI antiserum was produced in rabbits and used in established ELISA and dot immunobinding procedures against a 50 mM Tris/HCl, pH9.5 extract of freeze-dried leaf material from the CpTI+5 and CpTI−2 plants, using commercial beta-galactosidase or horseradish peroxidase linked goat anti-rabbit IgG as the secondary antibody, and an appropriate chromogenic substrate to measure antibody binding. Extracts from the resistant plants all have detectable levels of CpTI antigen in them, whereas those from the control (CpTI−2) plants do not. Trypsin inhibitory activity has been demonstrated directly in ammonium sulphate fractions of leaf extracts from the resistant plants by trypsin activity inhibition assays. The level of CpTI activity observed is comparable to that demonstrated to be anti-metabolic when incorporated into artificial diets.

A large proportion of the plants transformed with the vector described will contain, stably inserted into their genome, a fragment of DNA containing both a CpTI gene and the NPTII marker gene.

TABLE 2

Results of preliminary bioassays on transformed tobacco plants.

| | Damage[1] | % leaf eaten | No. larvae surviving[3] | Total size larvae[3] | ELISA[4] | TI activity assay[4] | Repeat trial No. larvae surviving[3] | Repeat trial Total size larvae[3] |
|---|---|---|---|---|---|---|---|---|
| *N. tab.* | | | | | | | | |
| Control (n = 9) | 3.3 ± 0.6 | 7.5 ± 3.2 | 3.1 ± 1.2 | 17.9 ± 7.5 | 1.9 ± 1.9 | 670 ± 670$_{(n=5)}$ | 7.5 ± 2.5$_{(n=3)}$ | 22.0 ± 8.8 |
| CPTI + 5 (n = 21) | 2.8 ± 0.7 | 5.6 ± 3.7 | 2.3 ± 1.7 | 11.0 ± 9.0 | 6.5 ± 1.4 | — | 2.8 ± 1.9$_{(n=8)}$ | 8.1 ± 6.3 |
| +5/5 | 1.0 (+++) | 1.0 (++) | 1 (+) | 3.5 (+) | 9.1 (+++) | 3941 (+++) | 0(+++) | 0 (++) |
| +5/21 | 2.1 (++) | 4.1 (+) | 0 (+++) | 0 (++) | 8.9 (+++) | 2805 (+++) | 3 (+) | 7.5 (+) |
| +5/04 | 1.9 (++) | 4.1 (+) | 0 (+++) | 0 (++) | N.D. | 1527 (+) | 3 (+) | 6.2 (+) |

TABLE 2-continued

Results of preliminary bioassays on transformed tobacco plants.

|  | Damage[1] | % leaf eaten | No. larvae surviving[3] | Total size larvae[3] | ELISA[4] | TI activity assay[4] | Repeat trial | |
|---|---|---|---|---|---|---|---|---|
|  |  |  |  |  |  |  | No. larvae surviving[3] | Total size larvae[3] |
| N. plumb. |  |  |  |  |  |  |  |  |
| Control (n = 6) | 3.1 ± 0.4 | 40.2 ± 15.3 | 4.0 ± 0.6 | 24.1 ± 3.7 |  |  |  |  |
| CPTI + 5 (n = 11) | 2.7 ± 1.1 | 18.3 ± 11.3 | 3.5 ± 1.7 | 18.0 ± 10.2 |  |  |  |  |
| TI04 | 1.0 (+++) | 6.4 (++) | 1 (+++) | 3.0 (+++) |  |  |  |  |
| TI09 | 1.0 (+++) | 4.9 (++) | 1 (+++) | 3.5 (+++). |  |  |  |  |

Means and standard deviations of the sets of CpTI + 5 and control plants, and the results of individual plants showing clearly enhanced resistance to insects, are presented. Crosses in parentheses indicate a result which is better than the control mean by more than 1 × S.D. [(+), $p < 0.159$]; 1.96 × S.D. [(++), $p < 0.025$] and 2.58 × S.D [(+++), $p < 0.005$].
[1]Mean values for 6 (N. tabacum) or 2 (N. plumbaginifolia) independant assessments of overall damage to plants on a 1 (minimal damage) to 5 (extensive damage) scale.
[2]Measured on the third mature leaf from the apex
[3]7 days after infesting the plants with 8 newly emerged larvae
[4]Expressed as equivalent amount of purified CpTI fIV (run as standard) in ng/100 ul leaf extract. Note that ELISAs underestimate the absolute amount of trypsin inhibitor (TI) present, due mainly to poor cross-reactivity of the antiserum.

This was confirmed by the results of segregation analysis for kanamycin resistance and Southern blotting experiments.

The new phenotypic traits acquired through transformation ought to be inherited according to classic Mendelian genetics. The initial transformants are expected to be hemizygous at each genetic locus at which insertion has occurred, and the characters are expected to behave as Mendelian dominants. In order to validate stable expression of the new traits, $S_1$ (first generation of plants produced by self-pollination) progeny from transformed plants were analysed for kanamycin resistance and the expression of CpTI.

Alternative strategies to the one described could be used to obtain CpTI coding sequences, involving some or all of the following variations:

i) Synthetic oligonuclectides encoding other regions of the CpTI polypeptide could be used in addition to, or instead of, the mixed 14-mers (region C) described.

ii) Partial or full length cDNA clones (or synthetic oligonuclectides) could be used as probes to obtain copies of the genomic sequences which include members of the CpTI gene family from recombinant genomic DNA libraries prepared from V. unguiculata genomic DNA.

iii) The CpTI primary sequences could be used to specify chemically synthesised nuclectide sequences which would encode a member of the CpTI family.

The following illustrate the present invention:

(1) Isolation of polyadenylated RNA

Seeds were harvested from a commercial variety Of cowpea (Californian black-eye) as they were approaching maturity. The testa and embryos were removed sterilely from the cotyledons and the latter were frozen in liquid nitrogen.

10 g of frozen cotyledons were warmed to −20° C. in a tube containing 0.2 g DTT, to which was added 26 ml 0.2M Na borate, pH9.0, 30 mM EGTA, 1% SDS at 100° C. The mixture was blended in a Polytron at Mk 5 for 30 sec then incubated with 0.5 mg/ml Proteinase K at 37° C. for 1 hour. 2 ml of 2M KCl was added at 0° C. and the mixture centrifuged. The supernatant was made 2M with respect to LiCl and insoluble material precipitated at 4° C. overnight.

The precipitate was pelleted by centrifugation, rinsed twice with 25 ml LiCl at 0° C., resuspended in 0.2M KAc and ethanol precipitated.

The precipitate was resuspended in 8 ml of 10 mM Tris-HCl, pH7.4, 1 mM EDTA and twice deproteinised with an equal volume of phenol/chloroform iso-amyl-alcohol (25:25:1). The final aqueous phase was ethanol precipitated and the RNA once more precipitated from 0.2M KAc prior to isolation of the polyadenylated RNA by oligo(dT)-cellulose column chromatography as described by Aviv and Leder (Aviv, H. & Leder, P. [1972] Purification of biologically active globin mRNA by chromatography on oligothymidylic acid cellulose. Proc. Natl. Acad. Sci. U.S.A. 59, 1408–12).

(2) Preparation of cDNA for cloning

Two alternative methods of cDNA synthesis were employed. The first method yielded the partial cDNA sequence cloned in pAGC1 and subsequently used as a probe for CpTI gene sequences, whereas the second, high efficiency method yielded near full-length cDNAs. Since both methods are capable of producing CpTI encoding sequences, both are described. The former procedure is detailed first.

(3) Synthesis of cDNA I

Reverse transcription of 5 ug cotyledon polyA+ RNA was carried out by incubating in a reaction mixture containing 50 uCi $^3$H-dCTP (50 Ci/mMol; Radiochemical Centre, Amersham, U.K.) as tracer, 1 mM each dATP, dCTP, dGTP & dTTP, 5 mM DTT, 1 mg/ml oligo (dT), 50 units human placental ribonuclease inhibitor, 50 mM Tris-HCl, pH 8.0, 10 mM MgCl$_2$ and 100 units/ml AMv reverse transcriptase at 42° C. for 2 h. The reaction was terminated and the strands separated by heating at 100° C. for 3 minutes and quenching at 0° C. Denatured proteins were removed by centrifugation.

(4) Second strand synthesis 45 ul of the reverse transcription reaction supernatant was incubated with 50 ul of 100 mM HEPES, pH 6.9, 20 mM MgCl$_2$, 70 mM KCl 5 mM DTT, 1 mM each dATP, dCTP, dGTP & dTTP and 25 units of DNA polymerase I large (Klenow) fragment at 15° C. for 4 h. The reaction mixture was extracted with phenol and chloroform and the high molecular weight reaction products separated by column chromatography on a 10 ml bed volume Sephadex (Trade mark) G-50-S column in 10 mM Tris-HCl, pH 7.4, 50 mM NaCl, 1 mM EDTA.

(5) Treatment of double stranded DNA ends for cloning

The excluded fraction from the above column was made up to a volume of 1 ml containing 0.3M NaCl. 30 mM NaAc pH4.5, 3 mM $ZnCl_2$ and incubated at 37° C. for 30 min with 250 units of $S_1$ nuclease to remove terminal loops. EDTA was added to 5 mM and the mixture extracted twice with phenol and chloroform, alcohol precipitated and resuspended in 20 ul of 50 mM Tris-HCl pH 7.8, 10 mM $MgCl_2$, 10 mM 2-mercaptoethanol, 0.25 mM each dATP, dCTP, dGTP & dTTP and incubated with 5 units DNA polymerase large fragment at 15° C. for 30 min to repair the ends.

Synthetic Bam HI linkers with the sequence 5'-d(GGGATCCC) [BCL] were phosphorylated in a volume of 10 ul containing 1 ug linkers, 50 mM Tris-HCl pH 7.8, 10 mM $MgCl_2$, 10 mM 2-mercaptoethanol, 1 mM ATP and 11 units polynuclectide kinase. This was incubated at 25° C. for 4 h.

The "polished" double stranded cDNA and kinased linkers were mixed, the volume adjusted to 50 ul with kinase reaction buffer and incubated with 5 units of T4 DNA ligase at 15° C. overnight.

The linker ligation reaction was terminated by incubation at 80° C. for 5 min. The reaction volume was adjusted to 200 ul containing 100 mM Tris-HCl pH7.4, 8 mM $MgCl_2$, and incubated with 10 units of restriction endonuclease Bst I at 37° C. for 8 h.

The reaction mixture was deproteinised by two extractions with an equal volume of phenol and twice with an equal volume of chloroform prior to loading on a 10 ml bed volume column of Sephadex G-50-S and elution in 10 mM Tris-HCl pH7.4, 50 mM NaCl, 1 mM EDTA. The excluded fraction from this column was used directly for ligation to the vector plasmid.

(6) Cloning into E. coli 910 using pBR322 as vector

Super-coiled plasmid pBR322 (GIBCO-BRL, Uxbridge, U.K.) was linearised by treatment endonuclease Bst I and partially dephosphorylated by treatment with calf intestinal alkaline phosphatase (in order to reduce self ligation of the vector ends) in accordance with established protocols.

Individual ligation reactions containing approximately 100 ng treated vector and an estimated 50 ng of "linkered" double stranded cDNA in 20 ul of 66 mM Tris-HCl pH7.6, 6.6 mM $MgCl_2$, 10 mM DTT, 0.5 mM ATP were incubated with 2 units T4 DNA ligase at 15° C. overnight.

3 ul aliquots of the ligation mixtures were diluted to a volume of 50 ul with 0.1M $CaCl_2$ and used to transform 100 ul batches of $CaCl_2$ treated E. coli strain 910 (obtained from Prof. W Brammar, Dept of Biochemistry, University of Leicester, U.K.) according to standard methods.

About 800 colonies resistant to ampicillin (50 ug/ml) were obtained per transformation. Copy plating these onto agar plates containing ampicillin or tetracycline (50 ug/ml) indicated that some 25% of these were ampicillin resistant, tetracycline sensitive, recombinants.

360 recombinant colonies were plated onto nitrocellulose filters and stored at −80° C. after replica filters had been prepared from them as described by Hanahan, D. & Meselson, M. ([1980] Plasmid screening and high colony density. Gene 10, 63-7) for screening by in situ hybridization.

(7) Screening of recombinants for CpTI coding sequence

As no single probe with absolute specifity for CpTI cDNA sequences was available, clones bearing such sequences were identified on the basis of a series of tests based on:
i) the expected abundance of CpTI mRNA in cotyledon RNA
ii) hybridization with a mixed synthetic 14-mer oligonuclectide complementary to the coding possibilities of region C Of the CpTI fIV polypeptide
iii) the size of the inserted sequence being close to that predicted for full-length CpTI cDNA
iv) direct determination of the inserted sequence to ensure it had the coding potential for (part of) a trypsin inhibitor.

Nitrocellulose filters bearing bacterial colonies which were to be used for hybridization were first incubated on agar plates containing 250 ug/ml chloramphenicol for 12-16 hours to allow amplification of the plasmid copy number. Filters were lifted from the plates and placed, colonies uppermost, on a series of pads of Whatman 3MM paper soaked in consecutively: 10% SDS for 3 min; 0.5M NaOH, 1.5M NaCl for 5 min; 1M Tris-HCl, pH 8.0, 1.5M NaCl for 5 min and 3×SSC (1×SSC=0.15M NaCl, 0.015M Na citrate) twice for 5 min. Filters were air dried and baked at 80° C. for 2 hours in a vacuum oven.

CpTI mRNA was predicted to be moderately abundant in cotyledon mRNA—its level more or less reflecting that of the protein, i.e. in the region of 1% of the total. 2 ug of cowpea cotyledon polyA. RNA was radiolabelled by reverse transcription in the presence of 50 uCi $^{32}$P-dCTP (410 Ci/mMol) as described in (3) above. High molecular weight reaction products were recovered from a Sephadex G-50-S column run in 10 mM Tris-HCl, pH 7.4, 1 mM EDTA. The $^{32}$P-labelled cDNA was preincubated in 10 ml of 3×SSC, 0.1% SDS, 0.02% each of bovine serum albumin (BSA), polyvinylpyrolidine (PVP) and Ficoll, 250ug/ml sonicated, dênatured salmon sperm DNA, 100 ug/ml polyadenosine at 65° C. for 1 h. Filters were prehybridized in 4 changes of 3×SSC, 0.1% SDS at 65° C. for 30 min each, then in 3×SSC, 0.1% SDS, 0.02% each BSA, PVP and Ficoll, 250 ug/ml sonicated denatured salmon sperm DNA at 65° C. for 4 h. The pretreated probe was added to the drained filters and incubated at 65° C. for 16 h. Filters were drained and washed with about 2 ml/om surface area of, sequentially, 3×SSC, 0.1% SDS twice for 5 min at room temperature, 3×SSC, 0.1% SDS thrice for 40 min at 65° C., 2×SSC twice for 5 min at room temperature: then dried and autoradiographed by exposure to Fuji RX X-ray film at room temperature for 19 h.

Some 30-40% of the colonies gave an autoradiographic signal of an intensity expected if they contained sequences which were moderately to highly repetitive in the probe.

A mixed oligonuclectide custom synthesis was carried out by Genex Corporation of all 16 alternatives of the 14-mers: 5'-dCC[A/G]CA[A/G]AA[A/G]CA[T/C]TG. The sequence was verified by established chemical modification sequencing procedures using reactions specific for T, T+C, C, A>C,A+G and G. Oligonuclectides were radioactively labelled at their 5'-ends by reaction with $^{32}$P-ATP using polynucleotide kinase in established procedures.

Nitrocellulose filters were preincubated in 3×SSC, 0.1% SDS four times for 30 min at 65° C., then in 6×SSC, 0.1% SDS, 0.02% each BSA, PVP and Ficoll, 1 mM EDTA, 125 ug/ml salmon sperm DNA at 45° C. for 8 h. Filters were hybridized with the labelled 14-mers in a similar mixture at 37° C. for 21 h. Filters were washed in 6×SSC, 0.1% SDS four times for 10 min at 25° C., then twice for 5 min at 39° C. They were rinsed in 6×SSC, dried and exposed to pre-flashed Fuji-TX film at −80° C. with a single Dupont Cronex intensifying screen for 21 h. Some 14% of the recombinants were clearly labelled above background.

Plasmid DNA was prepared from 10 ml cultures of 24 of the recombinants which were potentially CpTI cDNA positive on the preceding two criteria. The sizes of the inserted DNA sequences in these plasmids was determined from the migration of the Bam HI restriction fragments in agarose gel electrophoresis. Inserts ranged in size from about 400 to 1800 base pairs. Since CpTI cDNA was not expected to be longer than about 550 bp, the 4 clones containing inserts not longer than this were selected for sequence analysis. The Bam HI inserts of these clones were transferred to the Bam HI site of the single stranded bacteriophage vector M13mp9 and sequenced by dideoxy-chain termination with $^{35}$S-thio-dATP using established methods. The sequences obtained and their complements were examined for coding potential to give a product homologous to the primary sequence of CpTI fIV, of other legume Bowman-Birk type trypsin inhibitors and for homology with the published soybean Bowman-Birk trypsin inhibitor gene sequence (Hammond, R. W., Foarde, D. E., & Larkins, B. A. [1984] Molecular cloning and analysis of a gene coding for the Bowman-Birk protease inhibitor in soybean. J. Biol. Chem. 259, 9883–90).

Plasmid pAGC1 contained CpTI partial cDNA sequence presented above. Plasmid pUSSRa11/7 contained an identical coding sequence, lacking a further 6 nuclectides at the 5'end. The other two plasmids contained unidentified

(8) High efficiency cDNA synthesis

An improved method of cDNA synthesis was employed to obtain recombinants containing entire CpTI coding sequences. This method is more likely to produce full-length cDNAs as it does not depend on terminal loop priming of the second strand-synthesis and obviates the requirement for S1-nuclease digestion.

5.4 ug of cowpea cotyledon mRNA was incubated in 40 ul of: 50 mM Tris-HCl, pH 8.3; 10 mM MgCl$_2$; 10 mM DTT; 4 mM Na pyrophosphate; 1.25 mM each dATP, dCTP, dGTP and dTTP; 100 ug/ml oligo(dT) 12-18; 120 units AMV-reverse transcriptase; 40 units human placental RNase inhibitor and 2 uCi $^{32}$P-dCTP (as tracer) at 43° C. for 80 minutes. The reaction was stopped by transfer to melting ice and making it 20 mM with respect to EDTA, then twice deproteinised by phenol/chloroform extraction. Nucleic acids were ethanol precipitated from the aqueous phase previously made 2M with respect to ammonium acetate and 1 ug/ul with respect to highly purified oyster glycogen (as carrier). The pelleted nucleic acids were reprecipitated from 2M ammonium acetate and resuspended in 10 ul water.

The first strand synthesis products were incubated in 35 ul total volume containing: 20 mM Tris-HCl, pH 7.5; 100 mM KCl; 10 mM ammonium sulphate; 5 mM MgCl$_2$; 0.15 mM NAD; 50 ug/ml nuclease-free BSA; 40 uM dATP, dCTP, dGTP and dTTP; 8.5 units/ml E. coli RNase H; 230 units/ml DNA polymerase I; 10 units/ml E. coli DNA ligase at 12° C. for 1 hour then at 22° C. for a further hour. The reaction was terminated and the products processed as for the preceding reaction. To remove any remaining 3'-overhangs on the first strand, the double stranded cDNA was incubated in 25 ul of: 33 mM Tris-acetate, pH 7.9; 66 mM KAc; 10 mM MgAc; 0.5 mM DTT; dTTp: 2.5 units T4 DNA polymerase at 12° C. for one hour. The reaction products were processed as above.

(9) Cloning into E. coli JM83 using pUC19 a vector

Super-coiled plasmid pUC19 (GIBCO-BRL, Uxbridge, U.K.) was linearised by treatment with restriction endonuclease Hinc II and dephosphorylated by treatment with calf intestinal phsophatase in accordance with established protocols.

Blunt end ligation reactions containing approximately 100 ng treated vector and an estimated 20 ng of double stranded cDNA in 20 ul of: 66 mM Tris-HCl pH 7.5; 6.6 mM MgCl$_2$; 10 mM DTT; 0.5 mM ATP and 2 units T4 DNA ligase were incubated at 4° C. overnight. The ligation reactions were made up to 2M ammonium acetate and ethanol precipitated. They were redissolved in 10 ul of 0.1M CaCl$_2$ and used to transform 100 ul batches of competent E coli JM83 (obtained from Dr J. Messing, Dept of Biochemistry, University of Minnesota, U.S.A.) according to established methods. Recombinants were selected as white colonies on YT-BCIG-Ampicillin-agar plates. 283 recombinant colonies were replica plated onto nitrocellulose filters.

(10) Screening of recombinants for CpTI coding sequences

At this stage, cross-hybridization with both the pAGC1 insert and the synthetic 14-mer oligonucleotide was considered to be diagnostic of a CpTI cDNA sequence. DNA from the recombinant clones was fixed to the nitrocellulose filters as described above (Section 7). The pAGC1 insert was isolated from 2% agarose gel electrophoretic separation of Bam HI restriction fragments of pAGC1 and labelled with $^{32}$P-dCTP by nick-translation using a commercially available nick-translation kit. The synthetic 14-mers were $^{32}$P-labelled using polynucleotide kinase as previously described. Hybridisation to the colony filters was carried out as previously described, with the final stringency of washing being 2×SSC, 65° C. for the pAGC1 insert probe and 6×SSC, 39° C. for the synthetic oligonucleotides.

Plasmid pUSSRc3/2 hybridized very strongly to the pAGC1 insert, less strongly to the 14-mers, whereas pUSSRd4/6 hybridized very strongly to the 14-mers and less strongly to the pACG1 insert. Plasmid DNA was purified from these clones on caesium chloride gradients and restriction mapped according to established procedures. The nucleotide sequence of the inserted fragments was determined by chemical modification DNA sequencing.

Plasmid pUSSRc3/2 contained a virtually full-length cDNA sequence for a CpTI iso-inhibitor previously exemplified by pAGC1. Plasmid pUSSRd4/6 contained a cDNA sequence containing the entire coding sequence for the mature protein of a different CpTI iso-inhibitor, more closely related to the iso-inhibitor fIV but lacking part of the 5'-leader sequence.

(11) Transfer of pUSSRc3/2 CpTI coding sequences to an Agrobacterium BIN expression vector 10 ug of pUSSRc3/2 DNA was digested with restriction endonucleases Alu 1, Sca I and Xmn I in 33 mM Tris-acetate, pH 7.8; 66 mM KAc; 10 mM MgAc; 4 mM spermidine and 0.5 mM DTT (TA buffer). The unique 552 bp fragment generated, containing the entire CpTI coding sequence, was purified from a 6% acrylamide gel electrophoretic separation of the digest. The vector plasmid pRok2 (supplied by Dr. M. Bevan, Plant Breeding Institute, Cambridge, U.K.) was linearised with restriction endonuclease Sma I, dephosphorylated with calf intestinal phosphatase and blunt-end ligated to the 550 bp fragment as described above. The ligated reaction was used directly to transform E. coli strain MC1022 (Dr. M. Bevan, as above) to kanamycin (50 ug/ml) resistance.

Plasmid DNA was prepared from 10 ml cultures of individual transformed colonies and analysed for the uniqueness and orientation of the inserted fragment by restriction mapping. Clones with the insert in the correct orientation, i.e:

CaMV promoter - 5' CpTI coding sequence 3' - NOS terminator were designated pRokCpTI+ (clone number). Those in the wrong orientation, i.e.:

CaMV promoter - 3' CpTI coding sequence 5' - NOS terminator were designated pRokCpTI-(clone number)

(12) Transfer to Agrobacterium tumefaciens 10 ml overnight cultures were prepared of:

Agrobacterium tumefaciens strain LBf4404 (Dr. M. Bevan, as above) in nutrient broth+500 ug/ml streptomycin+100 ug/ml rifamycin at 30° C.;

E. coli strain MC1022 harbouring pRokCpTI+5, or pRokCpTI-2 in L-broth+50 ug/ml kanamycin at 37° C.;

E. coli HB101 harbouring pRK2013 (Dr. M. Bevan, as above) in L-broth+500 ug/ml streptomycin+100 ug/ml rifamycin at 37° C.

200 ul of each of the Agrobacterium, mobilizing strain and one of the CpTI containing strains were mixed, plated out on L-agar plates and incubated overnight at 30° C. The bacterial lawns were suspended in 5 ml Tris-HCl pH 7.0; 10 mM MgCl2 and aliquots plated out on minimal agar plates containing streptomycin (500 ug/ml, rifamycin (100 ug/ml) and kanamycin (50 ug/ml) and incubated at 30° C. for two days. The resistance of colonies to all three antibiotics was ensured by replating individual colonies on similar selective plates twice more.

(13) Transfer of CpTI gene to Nicotiana tabacum and Nicotiana plumbaginifolia Discs were punched from the leaves of axenic N. tabacum (var Samsun) and N. plumbaginifolia (an unnamed dihaploid variety obtained originally from Institut National de Reoherche Agronomique, Versailles, Paris, France) plants and incubated with an overnight culture of A. tumefaciens harbouring the Ti-RokCpTI plasmid constructs. The discs were blotted dry and transferred to plates of shoot regeneration medium according to published procedures (Fraley, R. T., Rogers, S. G., Horsch, R. B., Sanders, P., Flick, J., Adams, S., Bittner, M., Brond, L., Fink, C., Fry, J. E., Galluppi, G., Goldberg, S., Hoffman, N. L., Woo, S., Expression of bacterial genes in plants cells [1983] Proc. Natl. Acad. Sci. U.S.A. 80, 4803-7; Horsch, R. B., Fry, J. E., Hoffman, N. L., Eichholtz, D., Rogers, S. G., Fraley, R. T. [1985] A simple and general method for transforming genes into plants. Science 227, 1229-31) in the presence of carbenicillin (500 ug/ml) and kanamycin (100 ug/ml). Kanamycin resistant shootlets were transferred to root inducing medium containing carbenicillin and kanamycin. Replicates of individual rooted plants were obtained by shoot culture. Well rooted plantlets were potted up in 50:50 compost and Perlite and grown on in a Sherer growth cabinet under a 16 hour daylight regime at 25° C.

The plants appeared to be phenotypically normal in terms of growth habit, rate of growth, time to flowering, viability of seed etc. (see Table 3).

TABLE 3

Phenotypic characteristics of transformed plants compared to non-transformed controls.

|  | Control | +5/5 |
|---|---|---|
| Median time to flowering (day) | 104 | 108 |
| Mean plant height at flowering (cm) | 19.6 | 21.5 |
| Viability of seed (% germination) | 93 | 99 |

(14) Bioassays of insect resistance of transformed plants

Pupae of Heliothis virescens (f.) [Lep.; Noctuidae] the tobacco budworm or tomato budworm, were supplied by the U.S.D.A. (Brownsville, Tex., U.S.A.). On arrival in the U.K., the cultures were maintained at 25° C. with a 13 hour light day length. The larval stages were reared on an agar based diet containing alfalfa, haricot bean meal, wheatgerm and essential vitamins and minerals; adults were maintained on a vitamin supplemented honey solution.

Plants, about 12 cm tall in the case of N. tabacum and 8 cm in the case of N. plumbaginifolia, were contained within individual sealed plantaria within the growth cabinet. These were infested with eight 12-24 hour old H. virescens larvae (eight was found to be the optimal number for larval survival on control plants under these conditions). After 7 days on the plants, all surviving larvae were removed, anaesthetised in methyl acetate, preserved in Bouins fixative and measured. Damage to the plants was estimated by ranking the plants on an arbitrary 1-5 scale of visible damage and measuring the area eaten from a specified leaf (the third mature leaf from the apex, usually the most damaged). The results from this experiment are shown in Table 2. Data showing CpTI levels and % insect surivival on an individual plant basis is shown in Table 4. Plants showing a moderate to high level of resistance to the insects (together with some control plants) were subjected to further rounds of infestation with first or second instar larvae.

Feeding trials with H. virescens on clonal replicate plants

N. tabacum transformants +5/5, +5/21 and -2/8 were replicated by stem cuttings which were rooted in kanamycin containing agar in groups of 8 to 16 plants. These were grown on in compost until about 12 cm tall, then inoculated with 8 newly emerged H. virescens larvae per plant in sealed plantaria as detailed previously. After 7 days the surviving insects were removed (except from a few plants which were monitored over a longer period) and insect survival and growth were assessed as before. Damage to the plants was estimated as percent eaten from the leaves by image analysisi of the specified leaves using a 'VIP' image analyser and software supplied by Sightsystems Ltd. (Newbury, U.K.).

The results are summarised in Table 5. *H. virescens* larvae were subject to significantly higher mortality and significantly reduced growth on the CpTI expressing transformants +5/5 and +5/21. These plants also suffered less damage than the controls.

TABLE 4

Bioassay for insecticial activity of CpTI in transformed tobacco plants against *H. virescens*.

| Original plants | CpTI detected (ug/mg soluble protein) | Tryposin inhibitor actvity | % insect survival |
|---|---|---|---|
| −2/2 | <1 | | 100 |
| −2/4 | <1 | | 87.5 |
| −2/7 | <1 | | 100 |
| −2/8 | <1 | 1.7 | 87.5 |
| +5/1 | 1.1 | | 87.5 |
| +5/3 | 1.3 | | 100 |
| +5/4 | <1 | | 100 |
| +5/5 | 9.6 | 9.9 | 37.5 |
| +5/9 | 5.8 | | 62.5 |
| +5/11 | 3.8 | | 62.5 |
| +5/14 | 4.2 | | 75.0 |
| +5/19 | 2.5 | | 62.5 |
| +5/21 | 6.2 | 7.0 | 50 |
| +5/23 | <1 | | 100 |

Only those plants using in two feeding trials are recorded.
CpTI was detected using a dot immunobinding assay on soluble proteins extracted from recently fully-expanded leaves which were removed before infestation. Standards were affinity purified CpTI in control protein extracts rom untransformed plants.
trypsin inhibitor activity was measured in leaf soluble protein extracts, expressed as ug equivalent of affinity purified CpTi per mg leaf protein. The leaves for this assay were recently expanded ones from more mature plants (after bioassay).

TABLE 5

Feeding trials with *Heliothis virescens*.
(*) −p < 0.05; () p < 0.025; (*) p < 0.01

| Parameter | −2/8 | +5/5 | Significance |
|---|---|---|---|
| insect survival (%) | 58.65 | 41.96 | (*) |
| mean size survivors (mm) | 15.42 | 10.57 | (***) |
| live insect weight/plant (mg) | 236.4 | 63.9 | (***) |
| leaf area eaten (%) | 52.3 | 21.1 | (***) |
| | −2/8 | +5/21 | |
| insect survival (%) | 86.36 | 72.73 | (**) |
| mean size survivors (mm) | 12.50 | 10.54 | (***) |
| live insect weight/plant (mg) | 193.5 | 109.8 | (***) |
| leaf area eaten (%) | 49.6 | 30.1 | (***) |

Feeding trials with other insect pests

Feeding trials were carried out to test the effect of the CpTI gene in tobacco (+5/5) against a number of other important insect pests of cotton and cereals:

(a) *Heliothis zea*

Pupae of *H. zea* were obtained from the Glasshouse Crops Research Insitute (Littlehampton) and U.S.D.A. (Brownsville, Tex., U.S.A.) and maintained as described for *H. virescens*. Clonal replicates of +5/5 and −2/8 were infested with 8 newly emerged (<24 h old) larvae per plant and the bioassay conducted as above.

In early trials, only 16/192 larvae survived on the control plants (of. 10/224 on +5/5)—the mean number of survivors per plant being too close to zero to be useful. However, using somewhat younger plants (6 cm tall) survival on the controls reached 30% and meaningful comparisons could be made [Table 6]. The CpTI expressing plants were clearly more resistant to attack by, and survival of, *H. zea*.

(b) *Spodoptera littoralis*

Pupae of *S. littoralis* were obtained from May & Baker Ltd., Ongar Research Station, Essex, U.K. and maintained as described for *H. viresoens*. Clonal replicates of +5/5 and −2/8 were infested with 8 newly emerged (<12 h old) larvae and the bioassay conducted as above. Damage to the plants was more evident on the lower leaves with this species of insect and so it was from this region that leaves were taken for image analysis. As shown in Table 7, the CpTI expressing plants were again found to be more resistant to attack by, and survival of, young larvae of *S. littoralis*.

TABLE 6

Feeding trial of +5/5 with *Heliothis zea*
(*) −p < 0.05: (n.s.) - not significant.

| Parameter | −2/8 | +5/5 | Significance |
|---|---|---|---|
| insect survival (%) | 30.00 | 17.70 | (*) |
| mean size survivors (mm) | 10.38 | 9.29 | (n.s.) |
| live insect weight/plant (mg) | 51.4 | 32.2 | (n.s) |
| leaf area eaten (%) | 41.61 | 13.31 | (n.s) |

TABLE 7

Feeding trial of +5/5 with *Spodoptera littoralis*
(*) −p < 0.05; (***) p < 0.025: (n.s.) - not significant.

| Parameter | −2/8 | +5/5 | Significance |
|---|---|---|---|
| Insect survival (%) | 61.25 | 43.75 | (*) |
| mean size survivors (mm) | 14.39 | 14.70 | (n.s.) |
| live insect weight/plant | 323.5 | 265.1 | (n.s.) |
| leaf area eaten (%) | 27.24 | 10.40 | (***) |

It may be of interest that, although there was no significant difference between the mean sizes of the surviving insects, there appeared to be a marked difference in the distribution of the sizes. On the control plants the size distribution appeared to be continuous, whereas on the +5/5s it was bimodal, with modal sizes considerably smaller or rather larger than the mean. We consider it to be likely that the former are succumbing to the antimetabolic effects of CpTI, whereas the latter may have attained a sufficient size (perhaps through cannibalism in some cases) to be able to withstand its effects.

(c) *Manducoa sexta*

Eggs of *M. sexta* were provided by Dr. S. Reynolds (School of Biological Sciences, University of Bath, Bath, U.K.). Kanamycin resistant $S_1$ progeny of +5/5 and −2/8 plants were infested with 4 newly emerged larvae (less than 24 h old) and the bioassay conducted as above.

*M. sexta* larvae are considerably larger than other Lepidopterans tested and rapidly cause major destruction of control plants. For this reason it was necessary to reduce the number of insects used per plant and, rather than measuring damage to a specific leaf, it was necessary to estimate total damage to the plant. CpTI expressing plants were found to have increased resistance to this species of pest (Table 8).

TABLE 8

Feeding trial of +5/5 with *Manduca sexta*
(*) −p < 0.05; (***) −p < 0.01.

| Parameter | −2/8 | +5/5 | Significance |
|---|---|---|---|
| insect survival (%) | 82.14 | 64.29 | (***) |

TABLE 8-continued

Feeding trial of +5/5 with *Manduca sexta*
(*) —p < 0.05; (***) —p < 0.01.

| Parameter | −2/8 | +5/5 | Significance |
|---|---|---|---|
| mean size survivors (mm) | 26.68 | 22.72 | (*) |
| live insect weight/plant (g) | 1.00 | 0.46 | (***) |
| plant eaten (%) | 80.10 | 60.45 | (***) |

(16) Determination of CpTI expression in transformed plants

Methods for studying the expression of CpTI in transformed plant tissues depended either on various immuno-cross reaction techniques using anti-CpTI antiserum or on direct in vitro trypsin inhibitor activity assays.

(a) Preparation of rabbit anti-CpTI antiserum

Primary anti-CpTI antibody containing serum was produced in rabbits. CpTI was glutaraldehyde cross-linked to rabbit serum albumin (RSA). Rabbits were injected with 500 ul CpTI-RSA suspended in 500 ul Freunds Complete Adjuvant. Four further injections were administered at approximately weekly intervals of 500 ul CpTI-RSA suspended in 500 ul Freunds Incomplete Adjuvant. Finally, booster injections of 0.5 mg unmodified CpTI in phosphate-buffered saline and, three weeks later, 0.25 mg CpTI-RSA were administered prior to collection of the immune serum.

The difficulties encountered in raising this antiserum indicated that CpTI is a poor antigen. It should be remembered that the antibodies were produced against total CpTI, of which the iso-inhibitor encoded by pUSSRc3/2 is only a fraction. The most probable antigenic sites on the inhibitors occur in the variable regions of the polypeptides and so it is not known what proportion of the antibodies will, in fact, cross-react with the introduced CpTI gene product. These methods are likely, therefore, to underestimate the amount of a single CpTI iso-inhibitor when using total CpTI as standard.

(b) Preparation of plant-tissue protein-extracts

Crude protein extracts for some of the initial ELISAs, and for dot immunoblots were prepared from young growing leaves, from washed roots and from stem sections. These were removed, frozen in liquid air, ground to a powder and freeze dried. They were extracted overnight at 4° C. at 40 ug dry weight/ml of 50 mM Tris-HCl, pH 9.5 on a rotating wheel. Subsequent ELISAs, in vitro trypsin inhibitor assays and Western blots were performed on ammonium sulphate precipitate fractions. Leaves were harvested, frozen and ground as above. They were immediately extracted overnight at 4° C. in 50 mM Tris-HCl, pH 9.5; 1 mM DTT, at 1 mg wet weight/2.7 ul. Insoluble material was pelleted by centrifugation and 1 ml supernatant was precipitated with ammonium sulphate to 95% saturation at 4° C. overnight. Precipitated protein was pelleted, resuspended in 400 ul extraction buffer and dialysed against 50 mM Tris-HCl, pH 9.5. Protein concentrations were determined using the Bradford protein assay (Bradford, M. M., [1976] A rapid and sensitive method for the quantitation of milligram quantities of protein utilising the principle of protein-dye binding. Anal. Biochem. 72, 248–54).

(c) Enzyme linked immunosorbent assays (ELISA)

CpTI expression was measured by ELISA of leaf extracts from transformed plants using a commercially available, peroxidase-linked secondary-antibody ELISA kit. The results of these assays were sufficient to allow qualitative identification of high expressing plants, but were considered to be quantitatively rather unreliable, resulting from the poor antigenicity of CpTI and the low levels of protein which could be bound to the ELISA plates.

(d) In vitro trypsin inhibitor assays

Trypsin inhibitory activity in the samples was determined using -N-benzoyl-DL-arginine-p-nitroanilide HCl (BAPNA) as substrate based on the method of Erlanger, et al. (Erlanger, B. F., Kakowsky, N., Cohen, W. [1961] The preparation and properties of two new chromogenic substrates of trypsin. Arch. Biochem. Biophys. 95, 271–278). The level of CpTI activity determined by this method was much higher than indicated by ELISA (Table 2)—much more in line with that expected to account for the observed biological activity. This assay method was, however, also subject to uncontrollably variable interference.

(e) Protein dot immunoblot assays

Tissue extracts containing 5 ug protein were bound to nitrocellulose filters and subjected to the dot immunobinding assay as described by Jahn, R., Schiebler, W., Greengard, P. ([1984] A quantitative dot-immunobinding assay for proteins using nitrocellulose membrane filters. Proc. Natl. Acad. Sci. U.S.A. 81, 1684–87), using $^{125}$I-donkey anti-rabbit antibody. Standards of known amounts of purified CpTI were co-loaded in 5 ug untransformed tobacco extracts. Following, autoradiography, quantitation was done either by scintillation counting of the individual 'dots' or by scanning the autoradiograph with an LKB Ultrascan integrating laser densitometer.

The results using this method were quite reproducible. The estimated level of about 0.9% total protein as CpTI in +5/5 is still probably an underestimate due to the poor cross-reactivity of the antibody.

Levels of CpTI expression in young and old leaves, stem and root tissue were estimated by this method. In this particular experiment a high level of 'background' nonspecific antibody binding limitted the level of reliable detection to about 18 mg per sample (0.4% protein) and contributed to an unusually low estimate of the level of expression in young leaves of +5/5s. The results (Table 9) clearly demonstrate, however, that:

the relative amount of CpTI decreases as the leaves mature;

CpTI is present in the stems of transformed plants;

it is expressed as an even higher proprotion of the total protein in roots.

TABLE 9

Expression of CpTI as percent of soluble protein in different plant tissue extracts.

| | Young leaf | Mature leaf | Stem | Root |
|---|---|---|---|---|
| +5/5 | 0.6 | <0.4 | 0.6 | 1.0 |
| −2/8 | <0.4 | <0.4 | <0.4 | <0.4 |
| Control | <0.4 | <0.4 | <0.4 | <0.4 |

(f) Western blots

Figure 8:
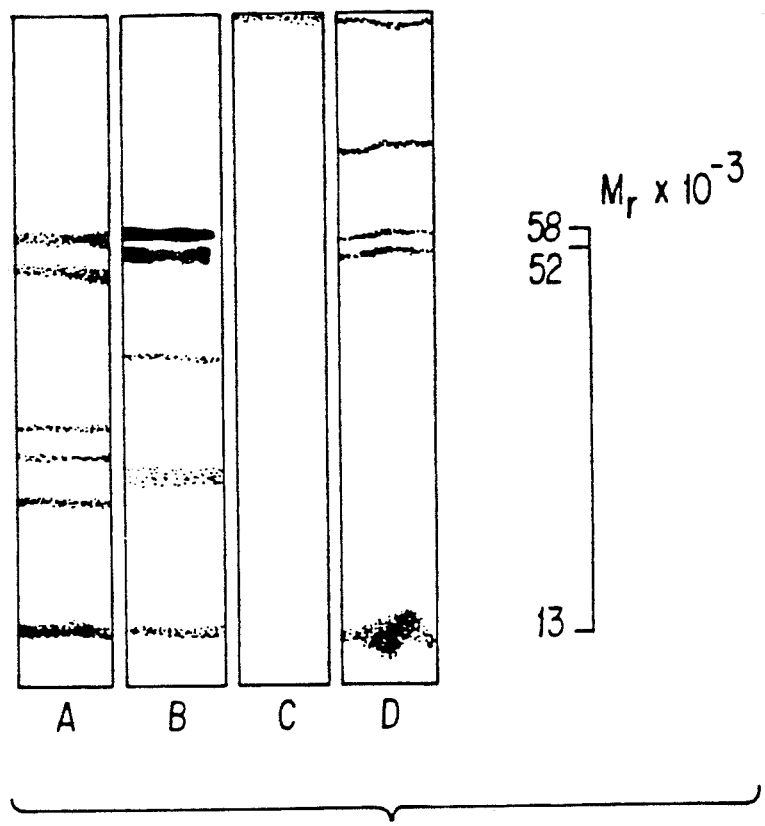
FIG. 8 is a Western blot analysis of CpTI expression in transformed *N. tabacum* leaf tissue.

The presence of CpTI in transformed tobacco plants was also confirmed by Western blotting. Ammonium sulphate Precipitated soluble protein extracts from young leaves of +5/5 and −2/8 plants were run on 17% polyacrylamide-SDS gel electrophoresis under non-reducing conditions. Trypsin-affinity column purified CpTI and soluble protein extracted from seeds of cowpea Tvu2027 were co-run as standards. Western blotting was performed as described by Towbin et al, (Towbin, H., Staehelin, T., Gordon, J., [1979] Electrophoretic transfer of proteins from polyacrylamide gels to nitrocellulose sheets. Procedure and some applications. Proc. Natl. Acad. Sci. U.S.A. 76, 4350–4). The blot (FIG. 8) shows that there are bands of CpTI antibody cross-reacting material present in the leaves of +5/5s which are absent in −2/8s and that these bands correspond with major bands of CpTI in the cowpea seed.

FIG. 9 shows the following:
A) Affinity purified CpTI
B) Seed extract of cowpea TVu2027
C) −2/8 leaf tissue
D) +5/5 leaf tissue

(17) Genetic analysis of transformants (a) Segregation analysis of kanamycin resistance The original *N. tabacum* transformed plants were allowed to set self pollinated seeds. Mature seeds were collected and stored in airtight bottles at 4° C. Seeds were surface sterilised in 20% "CHLOROS" and germinated on 0.8% agar containing 0.5×Murashige and Skoog medium salts, and 200 ug/ml kanamycin, in the growth cabinet.

Four types of phenotype were clearly distinguishable amongst the $S_1$ generation of seedlings:

Non-viable—seeds failed to germinate

Kanamycin resistant—which grew well on 200 ug/ml kanamycin, developing highly branched root systems and "healthy", green true leaves.

Kanamycin sensitive—seeds germinated but roots did not develop branches, true leaves failed to develop properly and cotyledons became bleached.

Intermediate resistance—seeds germinated and went on to develop true leaves, but the root system was clearly less branched than fully resistant seedlings (particularly evident when seedlings were pulled from the agar) and some patchy bleaching of the leaves was observed.

The viability of the seed from transformed plants was high—at least as high as that from untransformed *N. tabacum* (var. Samsum) germinated under similar conditions but excluding the kanamycin.

The results, summarised in Table 10 demonstrate that kanamycin resistance behaves as a simple Mendelian character, present at either one or two loci in the plants tested, giving rise to segregation ratios based on the classical Mendelian 3:1 or 9:3:3:1. The character is generally dominant, as expected, but appears to be of variable penetrance. Thus, the appearance of intermediate phenotypes in some of the two loci plants indicate that some of the loci are exerting a much stronger phenotypic effect than others. Note that the parental plants −2/2 and +5/19 would not have been propagated at this level of selection (which is twice the concentration of kanamycin which was initially used) and, indeed, line −2/2 has been lost on continous cultivation on 100 ug/ml kanamycin. As only one or two loci are involved, homozygous plants were identifiable in the $S_2$ generation.

TABLE 10

Segregation analysis of kanamycin resistance in the $S_1$ generation of transformed *N. tabacum* plants.
[*] in no case does, $\phi^2$ exceed the critical value.

| PLANT | NON-VIABLE | SEN-SITIVE | INTER-MEDIATE | RESISTANT | % GER-MINATION | SEGREGATION RATIO | $\phi^2$[*] | COMMENTS |
|---|---|---|---|---|---|---|---|---|
| +5/1 | 4 | 7 | — | 169 | 98 | (9 + 3 + 3):1 | 1.552 | 2 'strong' loci |
| +5/2 | 4 | 19 | — | 67 | 96 | 3:1 | 0.388 | 1 'strong' locus |
| +5/3 | 6 | 16 | — | 68 | 93 | 3:1 | 1.587 | 1 'strong' locus |
| +5/5 | 4 | 78 | — | 233 | 99 | 3:1 | 0.001 | 1 'strong' locus |
| +5/6 | 4 | 17 | — | 69 | 96 | 3:1 | 1.256 | 1 'strong' locus |
| +5/7 | 4 | 25 | — | 61 | 96 | 3:1 | 0.760 | 1 'strong' locus |
| +5/8 | 3 | 2 | — | 85 | 97 | (9 + 3 + 3):1 | 1.699 | 2 'strong' loci |
| +5/9 | 5 | 14 | — | 71 | 94 | 3:1 | 3.298 | 1 'strong' locus |
| +5/14 | 0 | 22 | — | 68 | 100 | 3:1 | 0.148 | 1 'strong' locus |
| +5/15 | 0 | 23 | — | 67 | 100 | 3:1 | 0.148 | 1 'strong' locus |
| +5/19 | 6 | 58 | 26 | 0 | 93 | 11:5 | 0.023 | 2 very 'weak' loci; requires three copies for even intermediate resistance at this level of selection |
| +5/21 | 8 | 13 | 31 | 128 | 96 | (9 + 3):3:1 | 0.859 | 1 'strong', 1 'weak' locus |
| +5/23 | 7 | 15 | — | 68 | 92 | 3:1 | 2.124 | 1 'strong' locus |
| −2/2 | 8 | 68 | — | 14 | 91 | 1:3 | 2.747 | 1 'weak' locus; requires 2 copies for resistance at this level of selection |
| −2/7 | 1 | 24 | — | 65 | 99 | 3:1 | 0.173 | 1 'strong' locus |
| −2/8 | 14 | 58 | 90 | 63 | 94 | 5:6:5 | 2.577 | 2 'weak' loci; >2 copies - resistant; 2 copies - intermediate; <2 copies - sensitive. |

(b) Inheritance of insect resistant phenotype

Ten of the kanamycin resistant $S_1$ progeny of +5/5 (designated +5/5[1] A11-20) were tested in the bioassay against *S. littoralis* (see Table 11) after which they were grown on and allowed to set self-fertilized, $S_2$ seed. This seed has been germinated on ½ MS agar containing 200 ug/ml kanamycin. $S_2$ seeds from 4/10 plants showed no segregation of the kanamycin resistant phenotype, tested, giving rise to segregation ratios based on expected from such a sample size. Interestingly, the 4 homozygous plants had been ranked 1st, 2nd, 3rd and 5th in terms of insect resistance in the bioassay.

(c) Southern blots

High molecular-weight genomic DNA was isolated from recently matured leaves of the transgenic plants by standard procedures. 10 ug of genomic DNA was digested overnight at 37° C. with 40 units each of Eco RI and Hind III and the restriction fragments separated by electrophoresis on 1% agarose gels. To provide 'marker' fragments and copy-number reconstructons, a mixture of pRokCpTI+5 and pRokCpTI−2 in a 5:1 ratio was digested with Eco RI and Hind III.

TABLE 11

| Feeding trial of $S_1$ plants (+5/5[1]) with $S.$ littoralis. (*) $-p < 0.05$; (**) $-p < 0.025$. | | | |
|---|---|---|---|
| Parameter | control | +5/5[1] | Significance |
| Insect survival (%) | 45.00 | 30.00 | (*) |
| Mean size survivors (mm) | 23.38 | 18.42 | (*) |
| Live insect weight/ plant (g) | 3.37 | 0.94 | (*) |
| Leaf area eaten (%) | 70.32 | 42.35 | (**) |

Restricted plasmid equivalent to 1,5 and 20 copies of the transferred sequences per Nicotiana genophore per 10 ug Nicotiana DNA were co-run. DNA was "Southern" transferred to nitrocellulose filters and probed with $^{32}$p-dCTP labelled, nick-translated, pRokCpTI+5. High stringency washing was carried out in 0.5×SSC, 0.1% SDS at 68° C. prior to autoradiography. The origin of the important bands on the autoradiographs of plants +5/5 and −2/8 are indicated in FIG. 9, in which (A) shows diagnostic restriction sites in pRokCpTI+5 and pRokCpTI−2 constructs, and (B) is an autoradiograph of a Southern blot.

The principal conclusions may be summarized as:
i) all the plants tested contain at least one unrearranged copy of the CaMV35S promoter-CpTI-NOS terminator construct, as indicated by the presence of 480 kp and 1200 kp bands in the +5s, and 610 and 1070 kp bands in the −2s.
ii) all contain multiple copies of the gene insert (see below)
iii) most copies are present in 'head to tail' tandem arrays—giving rise to a 2570 kp band. This insertion as tandem repeats accounts for the difference between gene copy-number and the number of genetic loci.
iv) bands which strongly suggest internal rearrangements within the constructs are uncommon, but identifiable in some plants.
v) the higher molecular weight bands are probably the result of:
   a) incomplete digestion
   b) 'end fragments' running into host DNA
   c) gene rearrangements
   d) transfer of the Ti-plasmid (d) Gene copy-number Copy-number was estimated from integrating laser-densitometric scans of the Southern blots and of genomic DNA dot blots using the plasmid DNA genomic copy-number reconstructions as standards. The results are presented in Table 12. It will be noted that there is no correlation between copy-number and CpTI expression (and hence, insect resistance). The nature of the site at which insertion occurred is, presumably, of more importance.

TABLE 12

| Copy-number of inserts in transformed plants. n.d. - not determined. | | |
|---|---|---|
| | Copies insert per genophore | |
| Plant | from Southern blots | from dot blots |
| +5/1 | 36 | 42 |
| +5/2 | 16 | 17 |
| +5/3 | n.d. | n.d. |
| +5/5 | 3 | 5 |
| +5/6 | n.d. | n.d. |
| +5/7 | 7 | 1 |
| +5/8 | 17 | 22 |
| +5/9 | 8 | 8 |
| +5/4 | 2 | 7 |
| +5/15 | 2 | 2 |
| +5/19 | 9 | 12 |
| +5/21 | n.d. | n.d. |
| +5/23 | 13 | 13 |
| −2/2 | n.d. | 3 |
| −2/7 | 3 | 6 |
| −2/8 | 7 | 13 |

What is claimed is:

1. A method of producing a transformed plant, comprising incorporating into the nuclear genome of the plant an isolated DNA which comprises a structural gene coding for a Bowman-Birk trypsin inhibitor from *Vigna unguiculata* and expresses said Bowman-Birk trypsin inhibitor from *Vigna unguiculata* in leaves, stems or roots of said transformed plant in an insecticidally-effective amount.

2. The method of claim 1, wherein said incorporating comprises transforming plant tissue or cells with a plasmid which comprises, from 5' to 3', a cauliflower mosaic virus 35S RNA promoter, a polylinker cloning site into which said structural gene has been inserted, and Agrobacterium transcription termination and mRNA polyadenylation signals.

3. The method of claim 2, wherein said plasmid is pROK2.

4. The method of claim 1, wherein said plant is of the genus Nicotiana.

5. The method of claim 4, wherein said plant is *Nicotiana Tabacum* or *Nicotiana plumbaginifolia*.

6. The method of claim 2, wherein said structural gene encodes a protein having a sequence selected from the group consisting of:
   (a) ($H_2$N)-?SGDHHQDFTDEPSE??EACCD-QCECTKSIPPQCRCSDVRLNSCHS ACK-SCACTFSIPAQCFCGDINDFCYKPCKSDSHD-D???-(COOH),
   (b) ($H_2$N)-SGDHHEATDEPSESSEACCDRCECT-KSIPPQCRCSDVRLNSCHS ACKSCACT-FSIPAQCFCGDIND-SCYKPCKSSSHDDDDWDK-(COOH), and
   (c) ($H_2$N)-SNHHDDSSDEPSESSEPCCDSCICT-KSIPPQCHCTDIRLNSCHS ACKSCMCTRSMPGKCRCLDIADF-CYKPCKSRDEDDE-(COOH),
where ? represents an amino acid residue at internal and C-terminal positions and a blocking group at an N-terminal position.

7. The method of claim 2, wherein said structural gene has the sequence:

```
AGTAATCATCATGATGACTCAAGCGATGAACCTTCTGAGTCTTCAGAACCATGCCTGCGATT
CATGCATCTGCACTAAATCAATACCTCCTCAATGCCATTGTACAGATATCAGGTTGAATTCG
TGTCACTCGGCTTGCAAATCCTGCATGTGTACACGATCAATGCCAGGCAAGTGTCGTTGCCT
TGACATTGCTGATTTCTGTTACAAACCTTGCAAGTCCAGGGATGAAGATGATGAGTAA
```

8. The method of claim 2, wherein said structural gene has the sequence:

```
GTGGTGATCATCATGAAGCAACTGATGAGCCCTCTGAATCTTCAGAAGCATGCTGTGATCGT
AGCGAATGCACAAAATCAATACCTCCTCAATGCCGCTGTCAGACGTAAGGCTCAATTCGTGC
CATTCAGCTTGCAAATCATGTGCCTGCACATTTTCCATTCCTGCACAGTGTTTTTGTGGTGA
CATAAACGACTCCTGCTATAAACCTTGCAAGTCCTCCAGTCATGATGATGATGACTGGGATA
AGTAA.
```

9. The method of claim 2, wherein said structural gene has the sequence:

```
GATGGCAAACATAGTACTATTATTTGATTTGTAATATGTACATAAAGAGCAGTGAGACCAAG
CCAATAACATCAGAAAATAAAAACTCAGGTACATTGACATTTATTCACCTTACACTGCAAAA
ACAAAAAAACTCTCAAGTTTGAAAACAAGATGATGGTGCTAAAGGTGTGTGTGCTGGTACTT
TTCCTTGTAGGGGTTACTACTGCAGCCATGGATTTGAACCACCTCGGAAGTAATCATCATGA
TGACTCAAGCGATGAACCTTCTGAGTCTTCAGAACCATGCCTGCGATTCATGCATCTGCACT
AAATCAATACCTCCTCAATGCCATTGTACAGATATCAGGTTGAATTCGTGTCACTCGGCTTG
CAAATCCTGCATGTGTACACGATCAATGCCAGGCAAGTGTCGTTGCCTTGACATTGCTGATT
TCTGTTACAAACCTTGCAAGTCCAGGGATGAAGATGATGAGTAAGAAAAAGGAAGATGAAGT
CTCTCTCTCAGATGAATAAAGCCCTTGAGTTTTGTTTGTTGTGTAAGGGAAGACAGAATAAA
AGTTGGAATAAAAGCTAGTGCTGTTCATC.
```

10. The method of claim 2, wherein said structural gene has the sequence:

```
GATGCACACCAAGCCCGAGCCTTCTGGGGACTTGTAGTGCTAGCTTGAAGGTGTCTGAGGTA
GGTCAAGTCATCAAAAGTGGTGATCATCATGAAGCAACTGATGAGCCCTCTGAATCTTCAGA
AGATGCTGTGCATCGTAGCGAATGCACAAAATCAATACCTCCTCAATGCCGCTGTTCAGACG
TAAGGCTCAATTCGTGCCATTCAGCTTGCAAATCATGTGCCTGCACATTTTCCATTCCTGCA
CAGTGTTTTTGTGGTGACATAAACGACTCCTGCTATAAACCTTGCAAGTCCTCCAGTCATGA
TGATGATGACTGGGATAAGTAATGAACAAGTTTAATGTAAGCTCTCTCTAAATGGATGAAGC
CCTTTCGGGCTTTGTTCGTTGTGTAATGAGATCAATAAACTTTGAATAAAAGCTCTTGTTTT
CGTGCC.
```

11. A transformed plant which contains and expresses a Bowman-Birk trypsin inhibitor from *Vigna unguiculata* in leaves, stems or roots in an insecticidally-effective amount, or an offspring of said transformed plant which contains and expresses a Bowman-Birk trypsin inhibitor from *Vigna unguiculata* in leaves, stems or roots in an insecticidally-effective amount.

12. The transformed plant of claim 11, prepared by incorporating into the nuclear genome of said plant an isolated DNA which comprises a structural gene coding for a Bowman-Birk trypsin inhibitor from *Vigna unguiculata*.

13. The transformed plant of claim 12, wherein said incorporating comprises transforming plant tissue or cells with a plasmid which comprises, from 5' to 3', a cauliflower mosaic virus 35S RNA promoter, a polylinker cloning site into which said structural gene has been inserted, and Agrobacterium transcription termination and mRNA polyadenylation signals.

14. The transformed plant of claim 13, wherein said plasmid is pROK2.

15. The transformed plant of claim 11, wherein said plant is of the genus Nicotiana.

16. The transformed plant of claim 15, wherein said plant is *Nicotiana tabacum* or *Nicotiana plumbaginifolia*.

17. The transformed plant of claim 11, wherein said Bowman-Birk trypsin inhibitor from *Vigna unguiculata* has a sequence selected from the group consisting of:

(a) (H$_2$N)-?SGDHHQDFTDEPSE?'EACCD-QCECTKSIPPQCRCSDVRLNSCHS ACK-SCACTFSIPAQCFCGDIND-FCYKPCKSDSHDD???-(COOH), (b) (H$_2$N)-SGDHHEATDEPSESSEACCDRCECT-KSIPPQCRCSDVRLNSCHS · ACKSCACT-FSIPAQCFCGDIND-SCYKPCKSSSHDDDDWDK-(COOH), and (c) (H$_2$N)-SNHHDDSSDEPSESSEPCCDSCICT-KSIPPQCHCTDIRLNSCHS ACKSCMCTRSMPGKCRCLDIADF-CYKPCKSRDEDDE-(COOH), where ? represents an amino acid residue at internal and C-terminal positions and a blocking group at an N-terminal position.

18. The transformed plant of claim 12, wherein said structural gene has the sequence:

```
AGTAATCATCATGATGACTCAAGCGATGAACCTTCTGAGTCTTCAGAACCATGCCTGCGATT
CATGCATCTGCACTAAATCAATACCTCCTCAATGCCATTGTACAGATATCAGGTTGAATTCG
TGTCACTCGGCTTGCAAATCCTGCATGTGTACACGATCAATGCCAGGCAAGTGTCGTTGCCT
TGACATTGCTGATTTCTGTTACAAACCTTGCAAGTCCAGGGATGAAGATGATGAGTAA.
```

19. The transformed plant of claim 12, wherein said structural gene has the sequence:

```
GTGGTGATCATCATGAAGCAACTGATGAGCCCTCTGAATCTTCAGAAGCATGCTGTGATCGT
AGCGAATGCACAAAATCAATACCTCCTCAATGCCGCTGTCAGACGTAAGGCTCAATTCGTGC
CATTCAGCTTGCAAATCATGTGCCTGCACATTTTCCATTCCTGCACAGTGTTTTTGTGGTGA
CATAAACGACTCCTGCTATAAACCTTGCAAGTCCTCCAGTCATGATGATGATGACTGGGATA
AGTAA.
```

20. The transformed plant of claim 12, wherein said structural gene has the sequence:

```
GATGGCAAACATAGTACTATTATTTGATTTGTAATATGTACATAAAGAGCAGTGAGACCAAG
```

-continued
```
CCAATAACATCAGAAAATAAAAACTCAGGTACATTGACATTTATTCACCTTACACTGCAAAA
ACAAAAAAACTCTCAAGTTTGAAAACAAGATGATGGTGCTAAAGGTGTGTGTGCTGGTACTT
TTCCTTGTAGGGGTTACTACTGCAGCCATGGATTTGAACCACCTCGGAAGTAATCATCATGA
TGACTCAAGCGATGAACCTTCTGAGTCTTCAGAACCATGCCTGCGATTCATGCATCTGCACT
AAATCAATACCTCCTCAATGCCATTGTACAGATATCAGGTTGAATTCGTGTCACTCGGCTTG
CAAATCCTGCATGTGTACACGATCAATGCCAGGCAAGTGTCGTTGCCTTGACATTGCTGATT
TCTGTTACAAACCTTGCAAGTCCAGGGATGAAGATGATGAGTAAGAAAAAGGAAGATGAAGT
CTCTCTCTCAGATGAATAAAGCCCTTGAGTTTTGTTTGTTGTGTAAGGGAAGACAGAATAAA
AGTTGGAATAAAAGCTAGTGCTGTTCATC.
```

21. The transformed plant of claim 12, wherein said structural gene has the sequence:

```
GATGCACACCAAGCCCGAGCCTTCTGGGGACTTGTAGTGCTAGCTTGAAGGTGTCTGAGGTA
GGTCAAGTCATCAAAAGTGGTGATCATCATGAAGCAACTGATGAGCCCTCTGAATCTTCAGA
AGATGCTGTGCATCGTAGCGAATGCACAAAATCAATACCTCCTCAATGCCGCTGTTCAGACG
TAAGGCTCAATTCGTGCCATTCAGCTTGCAAATCATGTGCCTGCACATTTTCCATTCCTGCA
CAGTGTTTTTGTGGTGACATAAACGACTCCTGCTATAAACCTTGCAAGTCCTCCAGTCATGA
TGATGATGACTGGGATAAGTAATGAACAAGTTTAATGTAAGCTCTCTCTAAATGGATGAAGC
CCTTTCGGGCTTTGTTCGTTGTGTAATGAGATCAATAAACTTTGAATAAAAGCTCTTGTTTT
CGTGCC.
```

\* \* \* \* \*